United States Patent [19]
Jackson et al.

[11] Patent Number: 5,871,483
[45] Date of Patent: Feb. 16, 1999

[54] FOLDING ELECTRODE STRUCTURES

[75] Inventors: Jerome Jackson; Dorin Panescu, both of Sunnyvale; David K. Swanson, Mountain View; Russell B. Thompson, Los Altos; James G. Whayne, Saratoga, all of Calif.

[73] Assignee: EP Technologies, Inc., Sunnyvale, Calif.

[21] Appl. No.: 629,171

[22] Filed: Apr. 8, 1996

Related U.S. Application Data

[60] Provisional application Nos. 60/010,223 Jan. 19, 1996; 60/010,225 Jan. 19, 1996 and 60/010,224 Jan. 19, 1996.

[51] Int. Cl.$^6$ .................................................. A61B 17/39
[52] U.S. Cl. .................. 606/41; 606/34; 607/99; 607/105; 607/113; 607/122; 600/374
[58] Field of Search ................. 606/41, 34; 128/642; 607/99, 105, 113, 122, 154; 600/374

[56] References Cited

U.S. PATENT DOCUMENTS

| | | |
|---|---|---|
| 4,979,948 | 12/1990 | Geddes et al. . |
| 5,195,969 | 3/1993 | Wang et al. . |
| 5,255,678 | 10/1993 | Deslauriers et al. . |
| 5,277,201 | 1/1994 | Stern ........................................... 606/41 |
| 5,293,869 | 3/1994 | Edwards et al. . |
| 5,311,866 | 5/1994 | Kagan et al. . |
| 5,334,193 | 8/1994 | Nardella . |
| 5,391,200 | 2/1995 | Kenknight et al. . |
| 5,462,545 | 10/1995 | Wang et al. . |
| 5,472,441 | 12/1995 | Edwards et al. . |
| 5,505,730 | 4/1996 | Edwards . |
| 5,562,720 | 10/1996 | Stern et al. . |
| 5,569,241 | 10/1996 | Edwards . |
| 5,598,848 | 2/1997 | Swanson et al. . |

FOREIGN PATENT DOCUMENTS

| | | |
|---|---|---|
| 0 080 536A | 6/1983 | European Pat. Off. . |
| 3516830 | 11/1986 | Germany ................................ 607/154 |
| 1220-673A | 3/1986 | U.S.S.R. . |
| WO95/01751 | 1/1995 | WIPO . |
| WO 96/00041 | 1/1996 | WIPO . |

OTHER PUBLICATIONS

Fann et al., Endocardial Activation Mapping and Endocardial Pace–Mapping Using a Balloon Apparatus, The American Journal of Cardiology, Apr. 1, 1995, pp. 1076–1083.

*Primary Examiner*—Lee Cohen
*Attorney, Agent, or Firm*—Lyon & Lyon LLP

[57] ABSTRACT

Improved folding electrode assemblies and associated methods employ a structure comprising a wall peripherally enclosing an interior. The structure is adapted to selectively assume a geometry that changes between an expanded geometry having a first maximum diameter and a collapsed geometry having a second maximum diameter less than the first maximum diameter. At least one folding region in the wall is adapted to fold upon itself along a predefined fold line as the structure geometry changes. The folding region is formed when a portion of the wall is coated with an electrically conductive material for the purpose of transmitting electrical ablating energy, while another portion of the wall is left free of the electrically conductive material. Alternatively, the folding region is formed by forming an array of apertures in the wall.

50 Claims, 18 Drawing Sheets

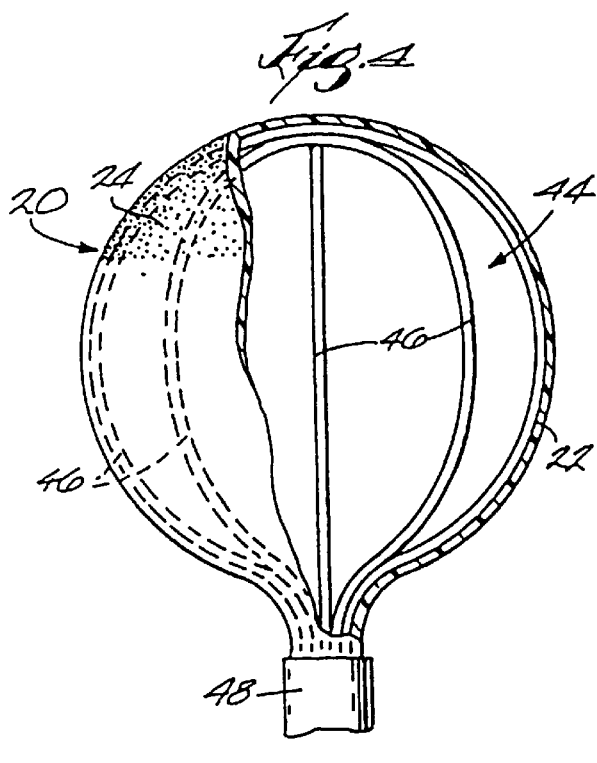
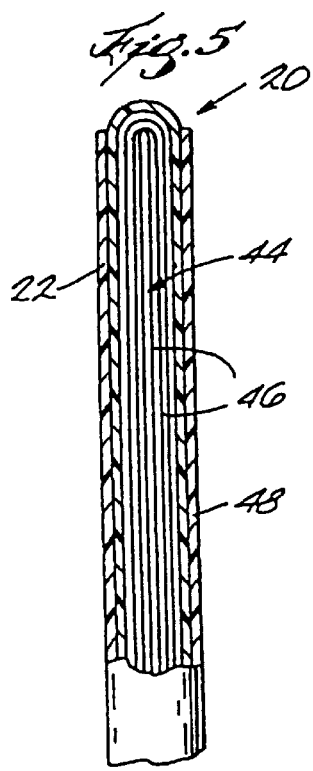
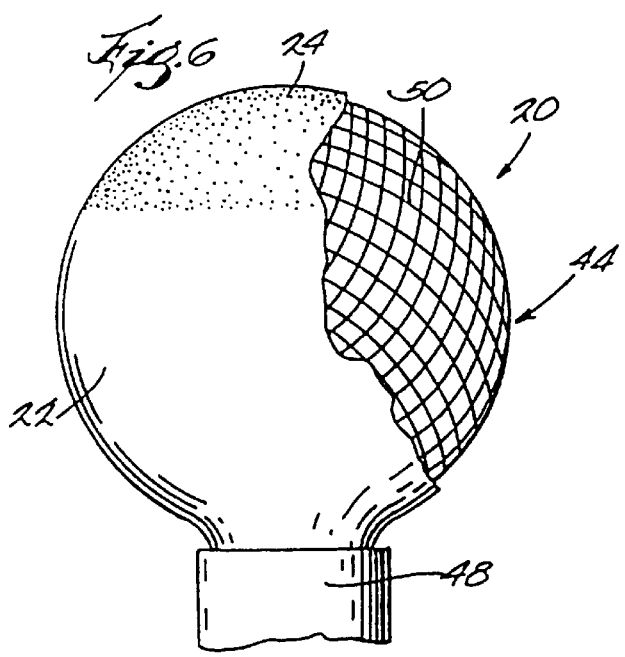
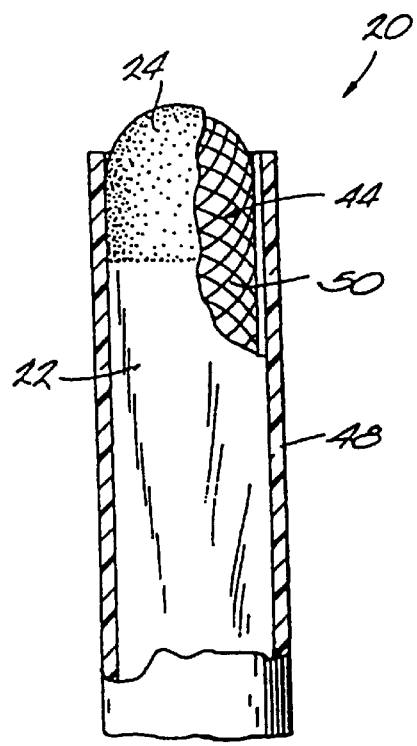

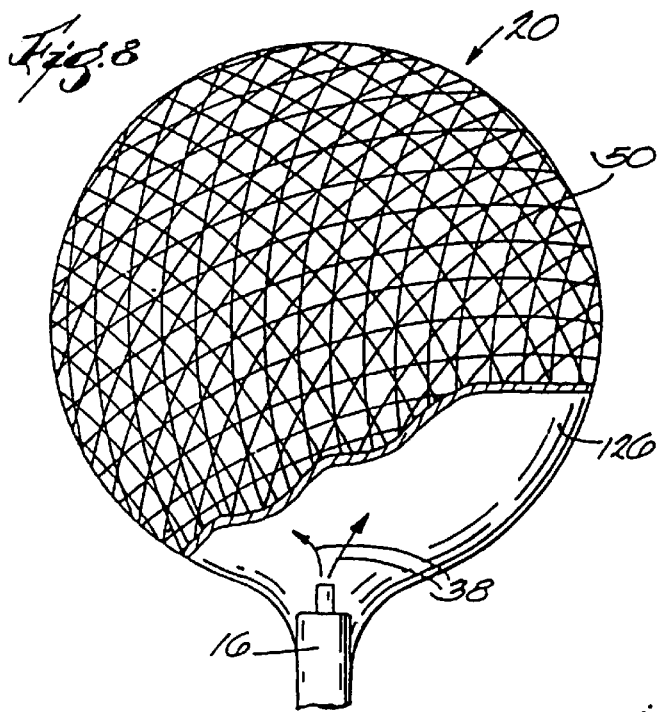
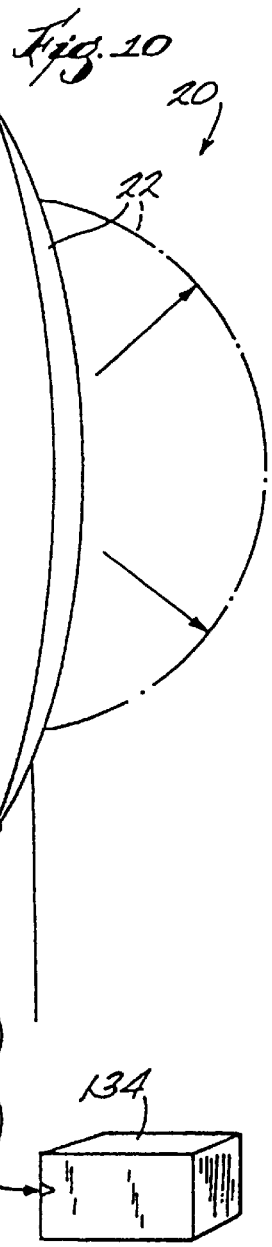
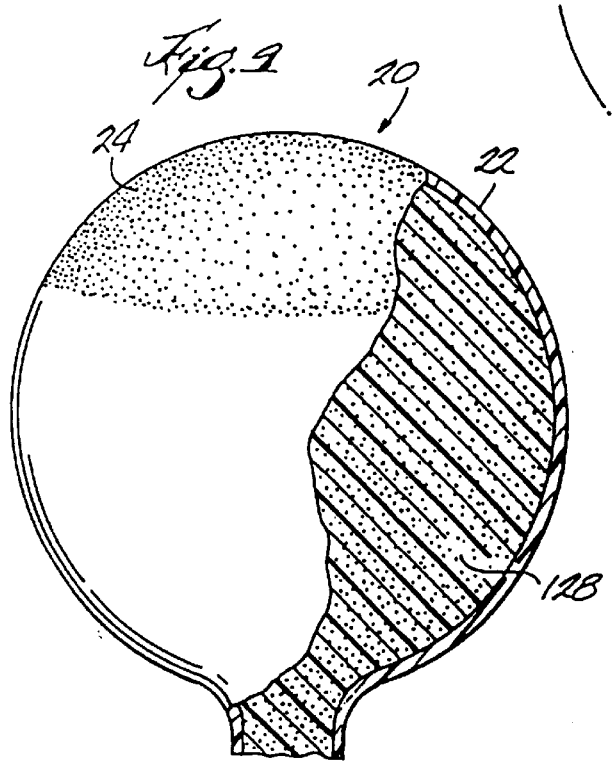

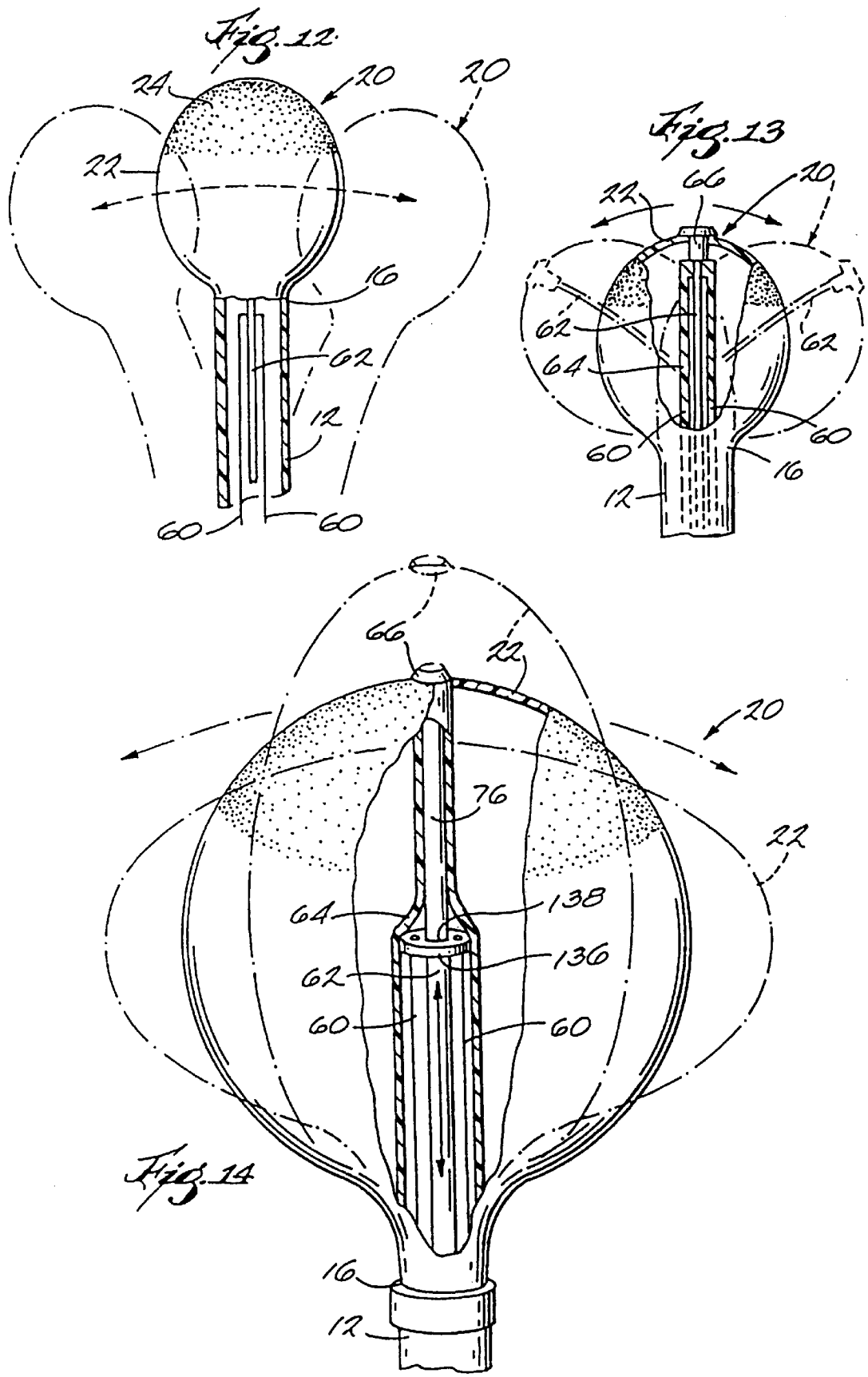

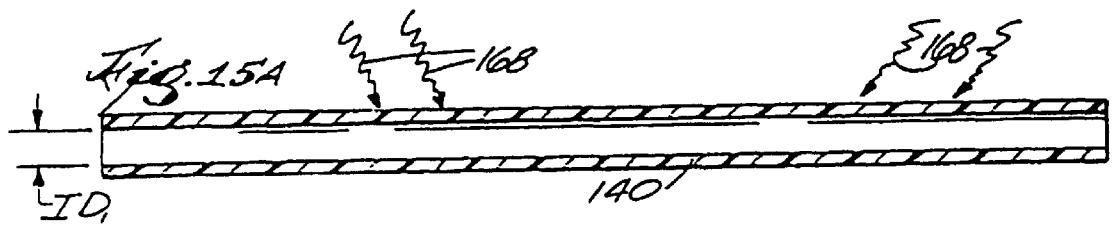
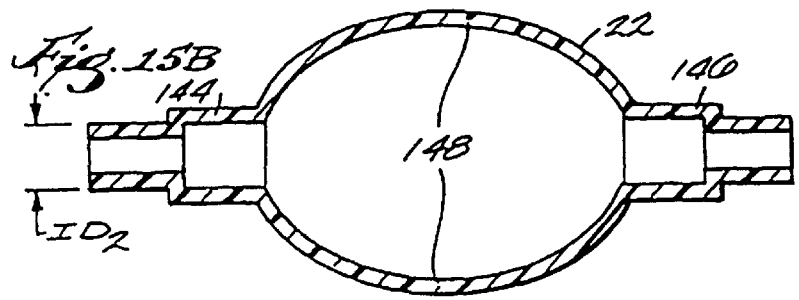
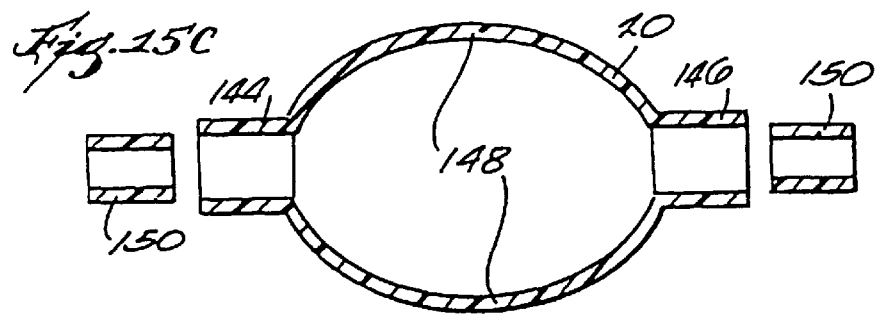
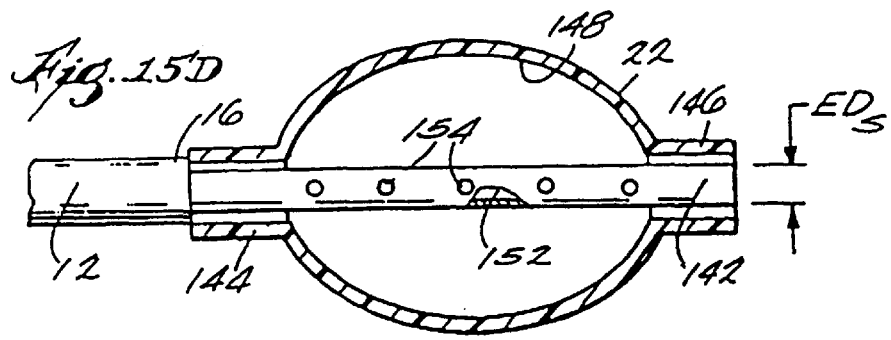
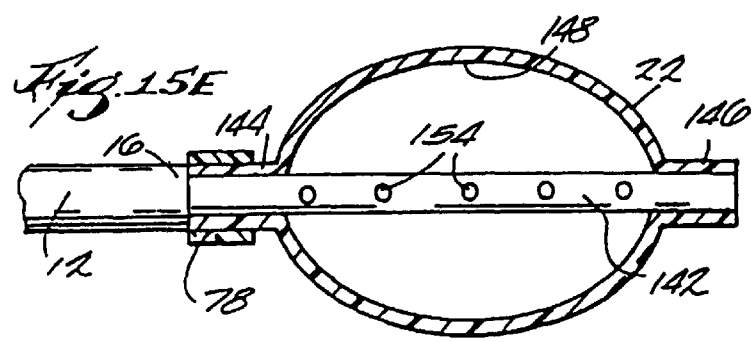

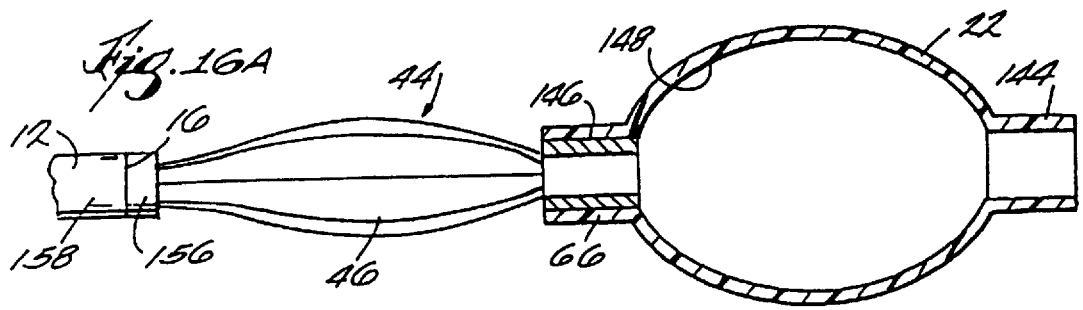
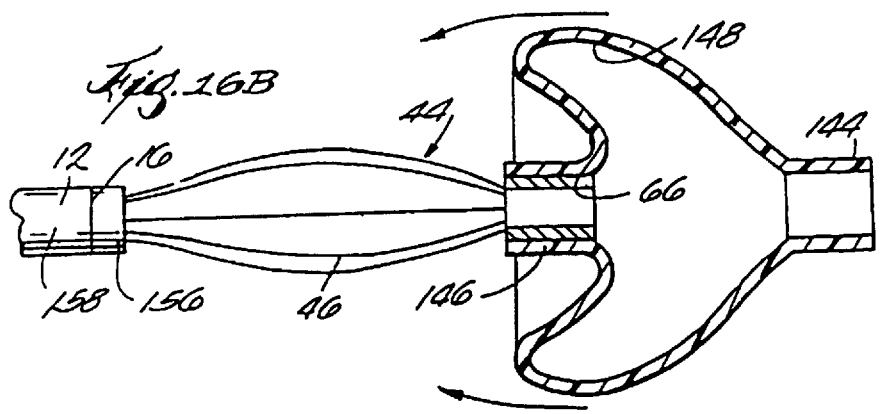
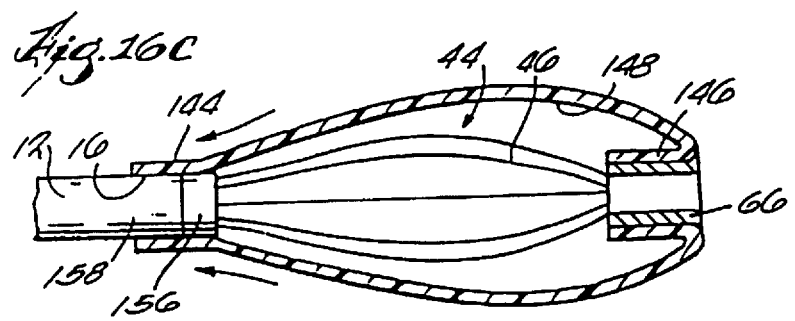
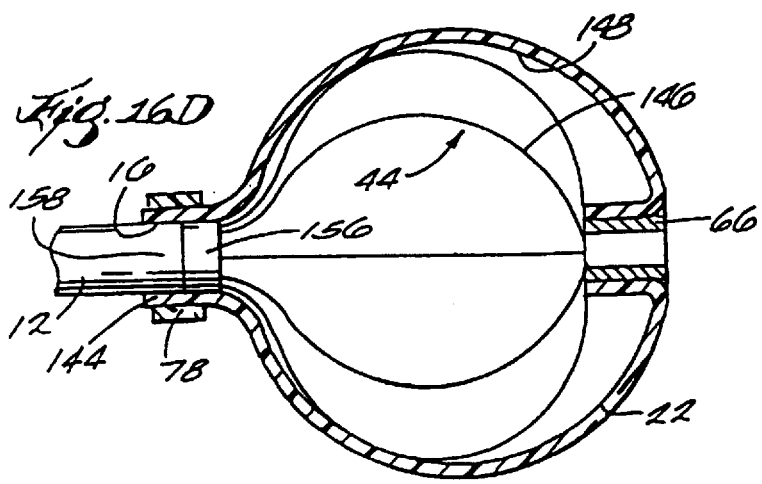

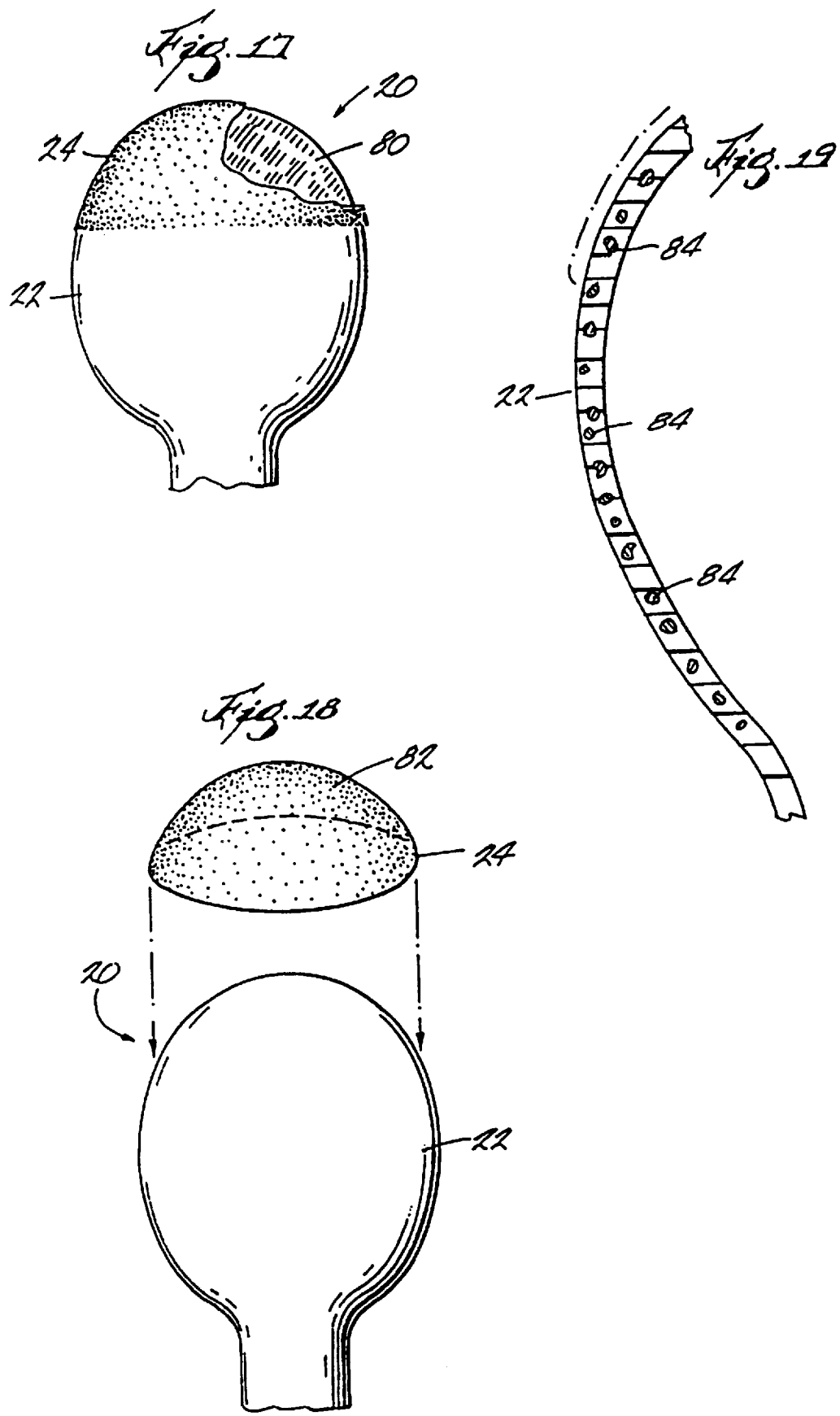

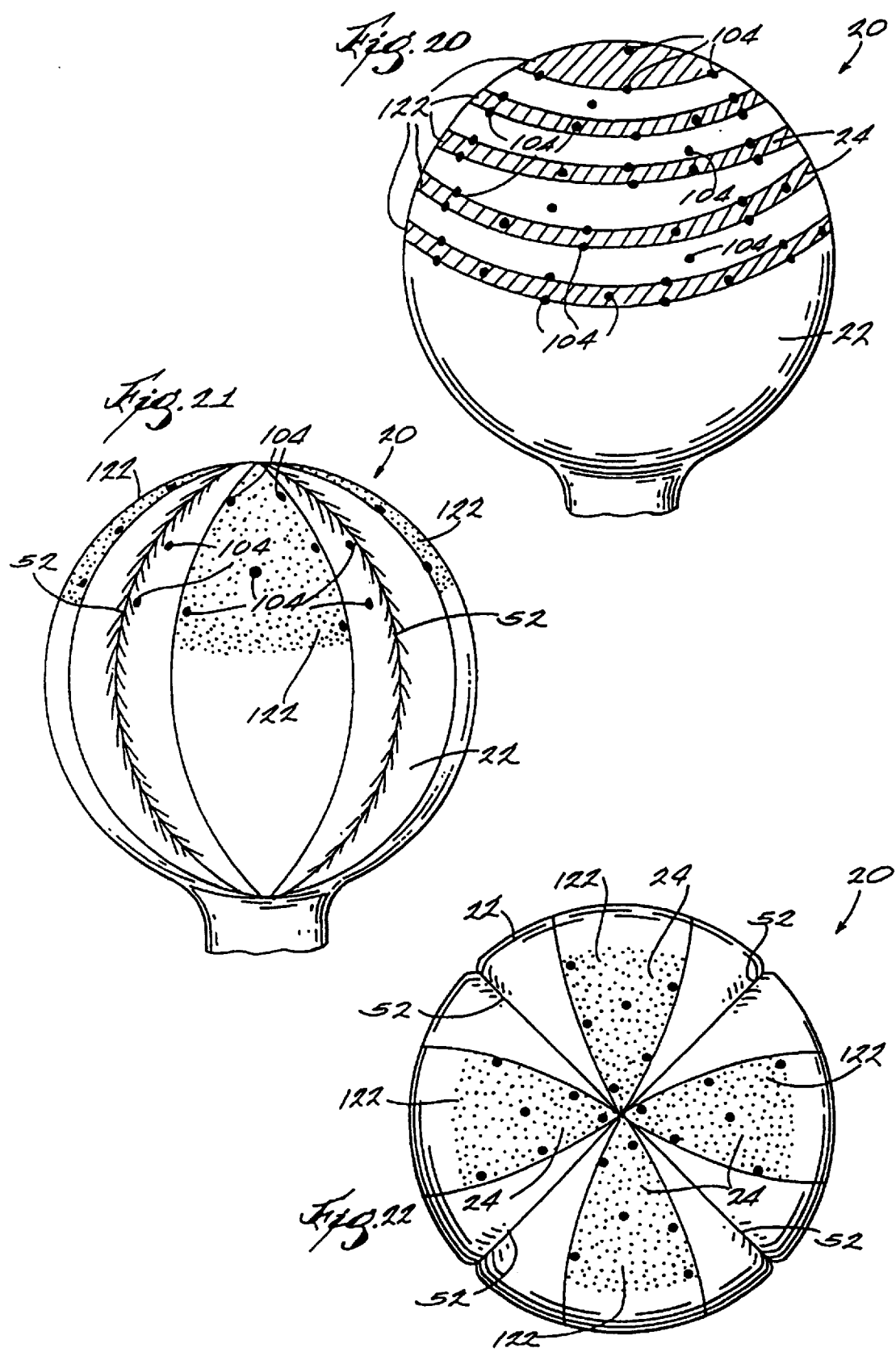

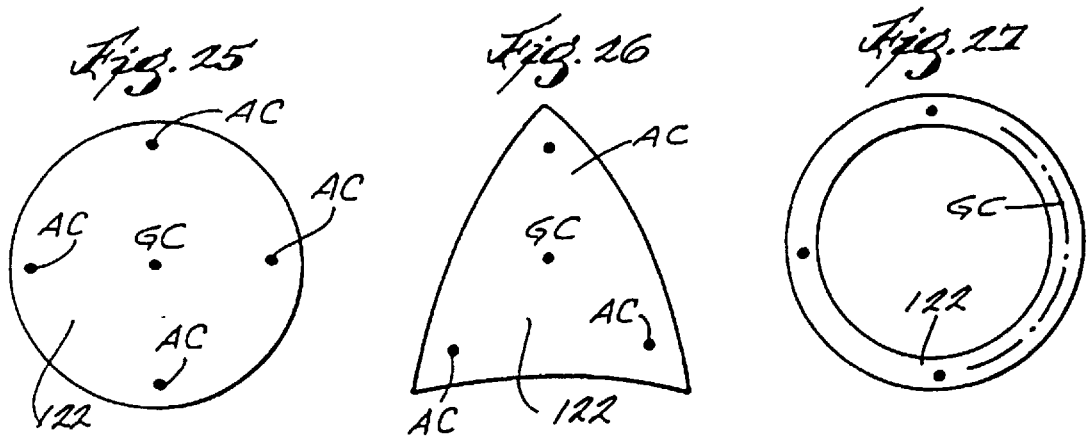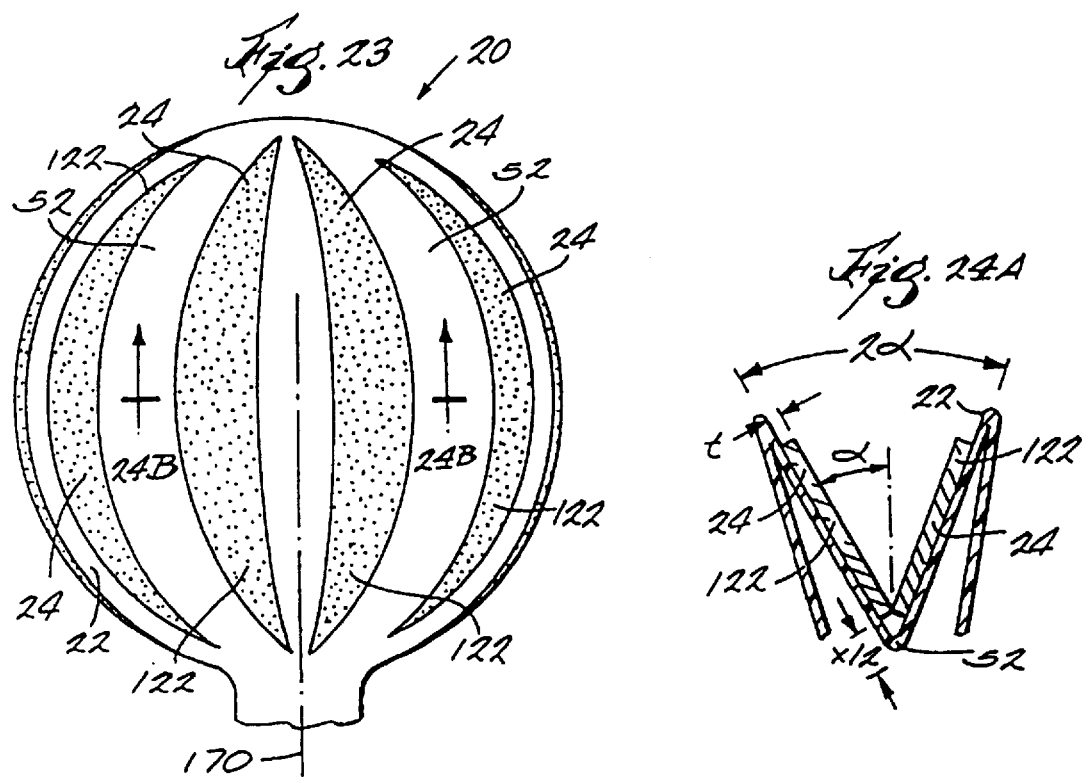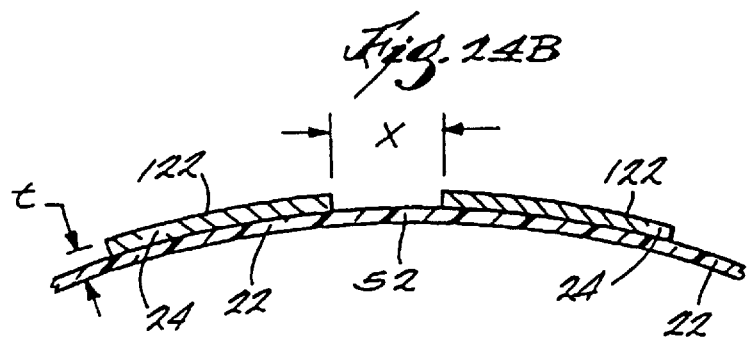

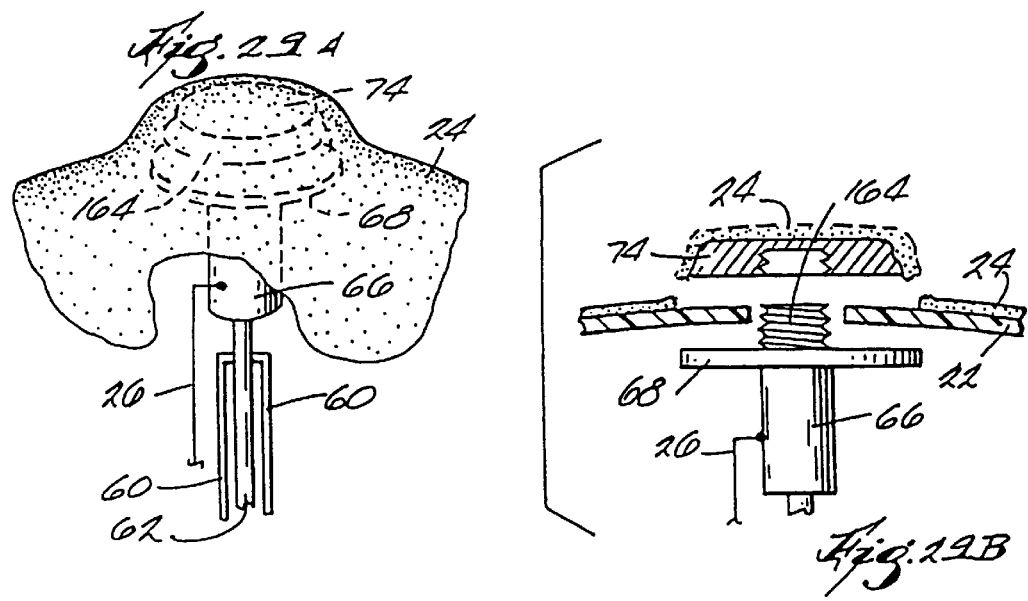
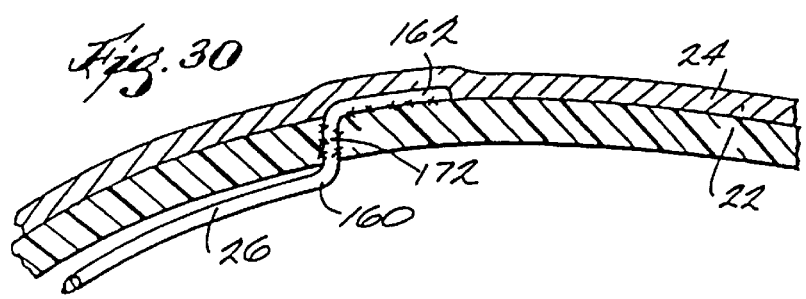
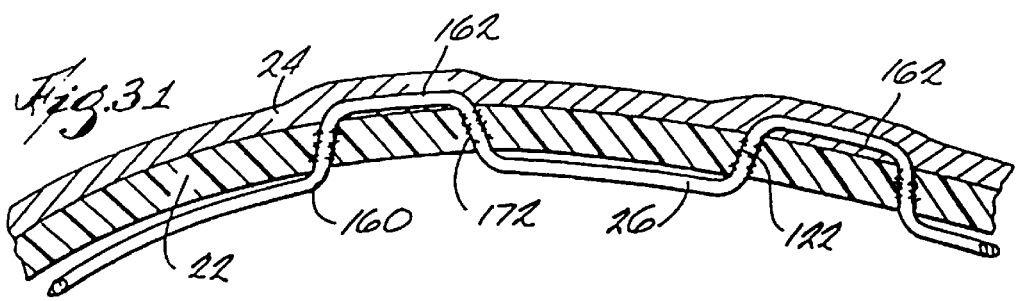
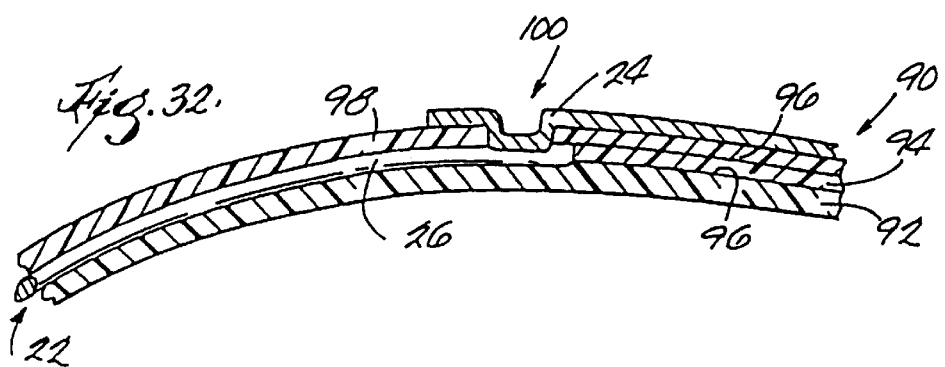

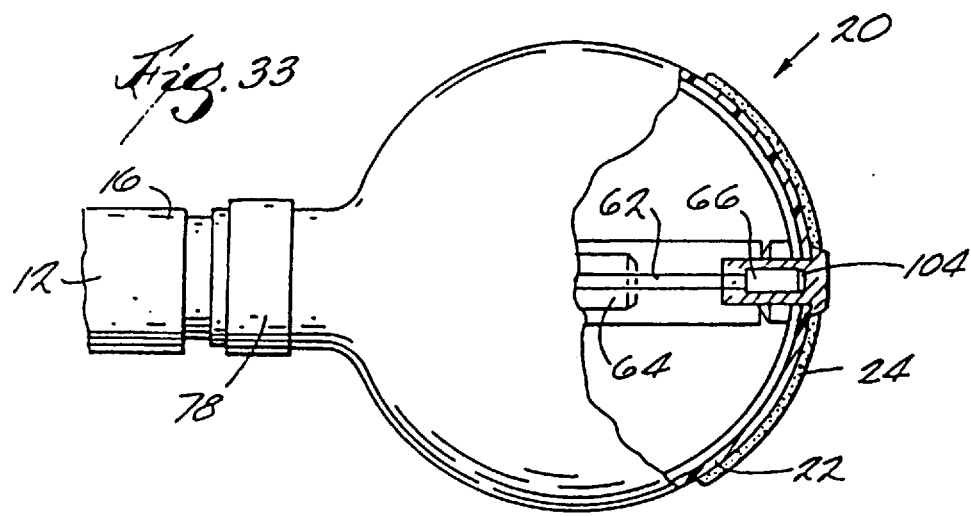
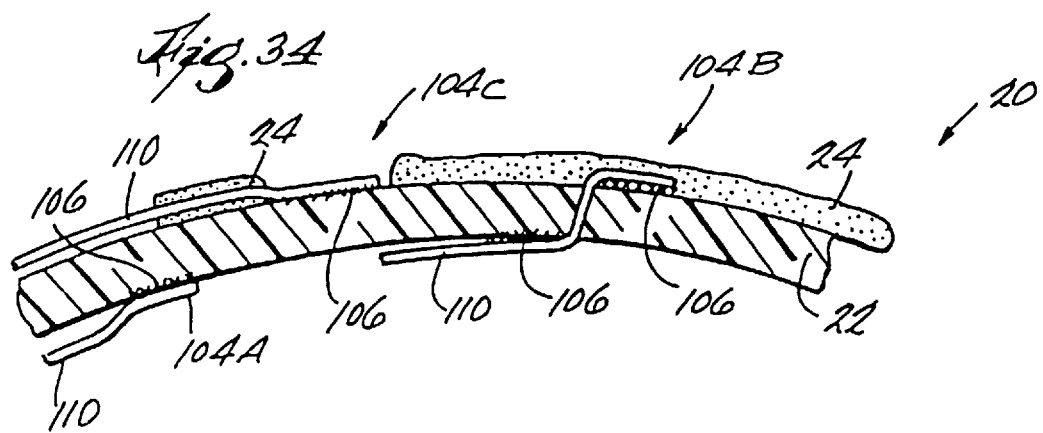
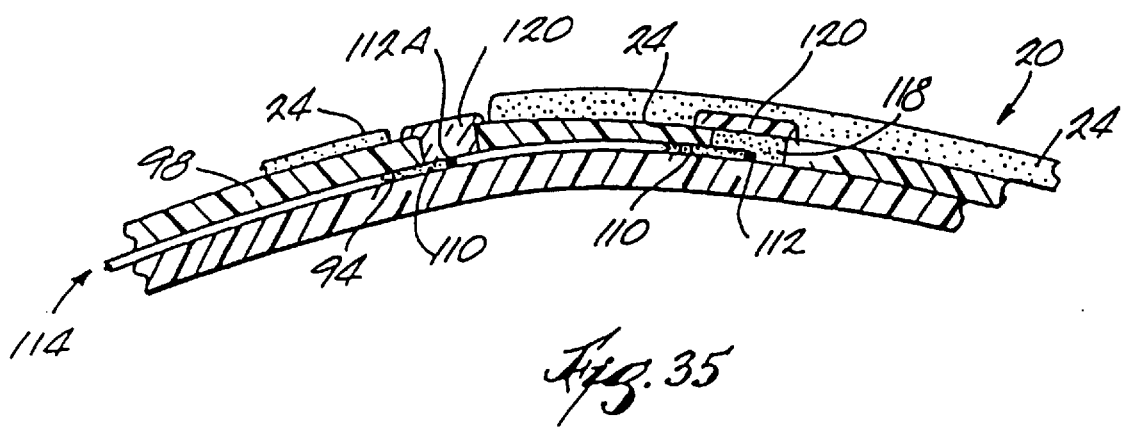

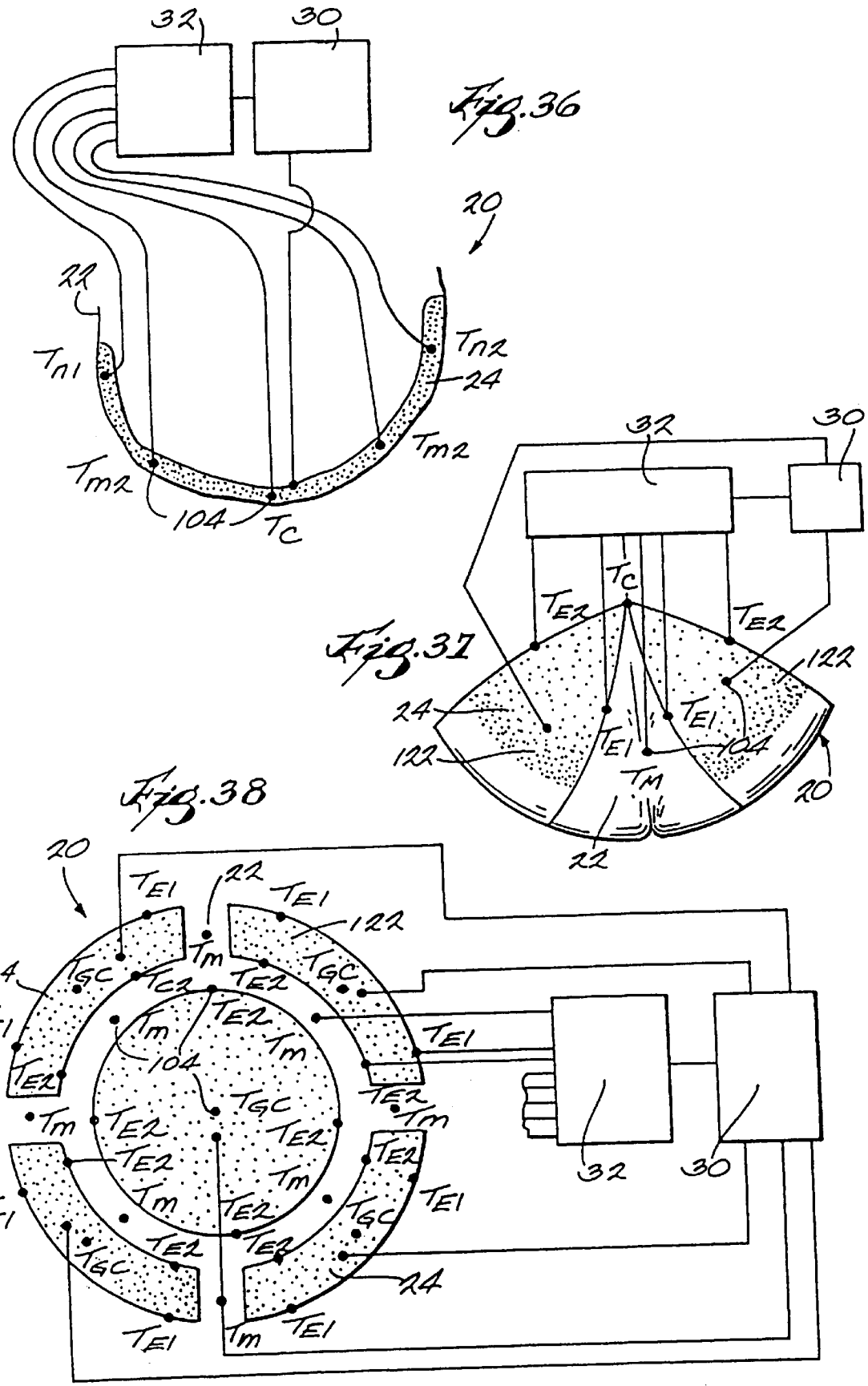

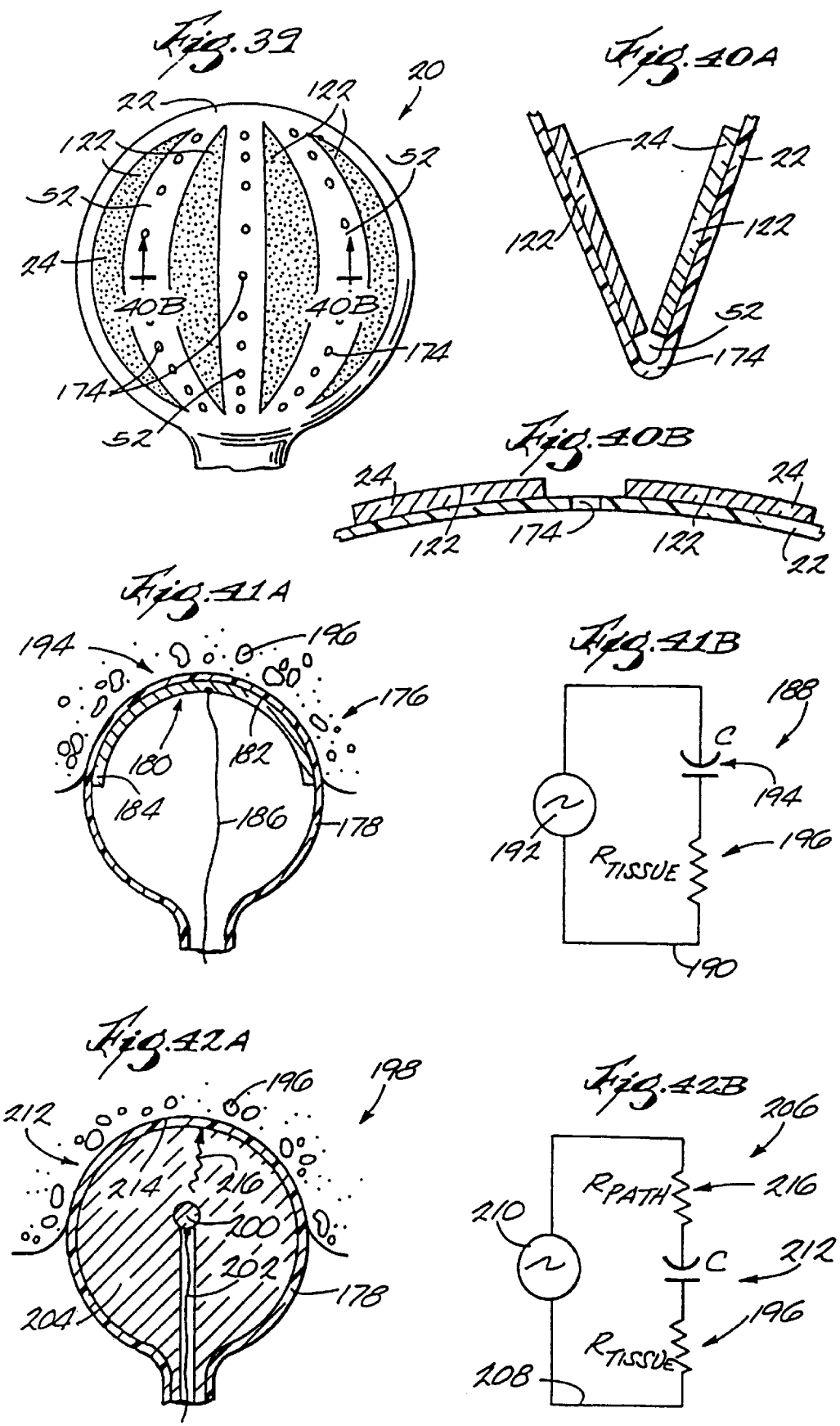

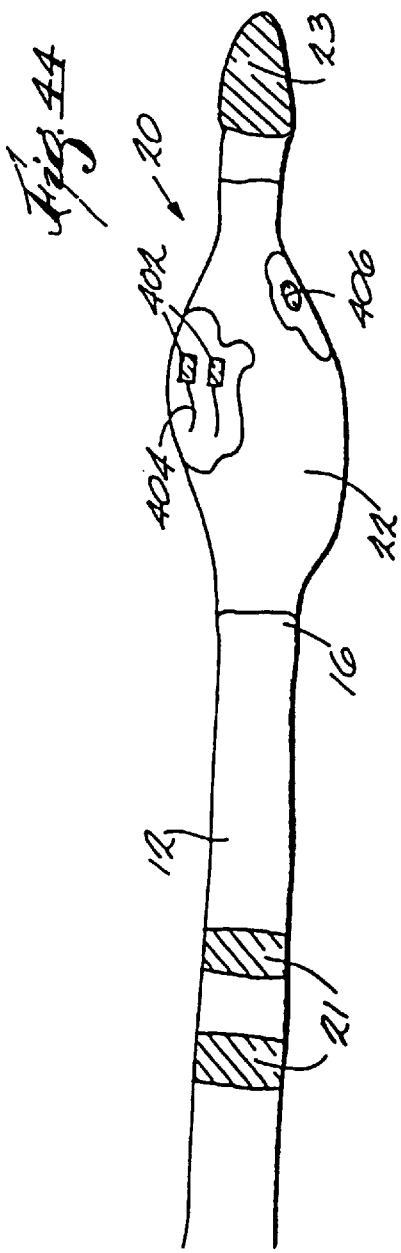

FOLDING ELECTRODE STRUCTURES

RELATED APPLICATION

This application claims the benefit of U.S. Provisional Applications having Ser. Nos. 60/010,223, 60/010,225 and 60/010,354, all of which were filed on Jan. 19, 1996.

FIELD OF THE INVENTION

The invention generally relates to electrode structures deployed in interior regions of the body. In a more specific sense, the invention relates to electrode structures deployable into the heart for diagnosis and treatment of cardiac conditions.

BACKGROUND OF THE INVENTION

The treatment of cardiac arrhythmias requires electrodes capable of creating tissue lesions having a diversity of different geometries and characteristics, depending upon the particular physiology of the arrhythmia sought to be treated.

For example, a conventional 8 F diameter/4 mm long cardiac ablation electrode can transmit radio frequency energy to create lesions in myocardial tissue with a depth of about 0.5 cm and a width of about 10 mm, with a lesion volume of up to 0.2 cm$^3$. These small and shallow lesions are desired in the sinus node for sinus node modifications, or along the AV groove for various accessory pathway ablations, or along the slow zone of the tricuspid isthmus for atrial flutter (AFL) or AV node slow or fast pathway ablations.

However, the elimination of ventricular tachycardia (VT) substrates is thought to require significantly larger and deeper lesions, with a penetration depth greater than 1.5 cm, a width of more than 2.0 cm, and a lesion volume of at least 1 cm$^3$.

There also remains the need to create lesions having relatively large surface areas with shallow depths.

One proposed solution to the creation of diverse lesion characteristics is to use different forms of ablation energy. However, technologies surrounding microwave, laser, ultrasound, and chemical ablation are largely unproven for this purpose.

The use of active cooling in association with the transmission of DC or radio frequency ablation energy is known to force the tissue interface to lower temperature values. As a result, the hottest tissue temperature region is shifted deeper into the tissue, which, in turn, shifts the boundary of the tissue rendered nonviable by ablation deeper into the tissue. An electrode that is actively cooled can be used to transmit more ablation energy into the tissue, compared to the same electrode that is not actively cooled. However, control of active cooling is required to keep maximum tissue temperatures safely below about 100° C., at which tissue desiccation or tissue boiling is known to occur.

Another proposed solution to the creation of larger lesions, either in surface area and/or depth, is the use of substantially larger electrodes than those commercially available. Yet, larger electrodes themselves pose problems of size and maneuverability, which weigh against a safe and easy introduction of large electrodes through a vein or artery into the heart.

A need exists for multi-purpose cardiac ablation electrodes that can selectively create lesions of different geometries and characteristics. Multi-purpose electrodes would possess the flexibility and maneuverability permitting safe and easy introduction into the heart. Once deployed inside the heart, these electrodes would possess the capability to emit energy sufficient to create, in a controlled fashion, either large and deep lesions, or small and shallow lesions, or large and shallow lesions, depending upon the therapy required.

SUMMARY OF THE INVENTION

The invention provides improved folding electrode assemblies and associated methods employ a structure comprising a wall peripherally enclosing an interior. The structure is adapted to selectively assume a geometry that changes between an expanded geometry having a first maximum diameter and a collapsed geometry having a second maximum diameter less than the first maximum diameter.

According to one aspect of the invention, an electrically conductive material having resistivity is carried by the wall. The electrically conductive material is adapted for transmitting ablation energy. The electrically conductive material conforms to both the expanded geometry and the collapsed geometry. The structure includes at least one folding region in the wall adapted to fold upon itself along a predefined fold line as the structure geometry changes. According to this aspect of the invention, the at least one folding region has resistivity that is greater than about ten times the resistivity of the electrically conductive material.

According to another aspect of the invention, at least two spaced apart coatings of electrically conductive material are applied to the wall. The coatings conform to both the expanded geometry and the collapsed geometry and are adapted for transmitting ablation energy. According to this aspect of the invention, the coatings are spaced apart by a predetermined distance (x) that, taking into account thickness (t) of the coatings, defines a folding region having a desired minimum fold angle (2α) when the structure is in its collapsed geometry, expressed as follows:

$$x \geq \frac{2t}{\tan\alpha}$$

According to another aspect of the invention, at least two spaced apart zones of electrically conductive material are also carried by the wall adapted for transmitting ablation energy. In this embodiment, an array of apertures in the wall between the spaced apart zones defines a folding region adapted to fold upon itself along a predefined fold line as the structure geometry changes.

In a preferred embodiment, cooling fluid is conveyed through the apertures.

Other features and advantages of the inventions are set forth in the following Description and Drawings.

BRIEF DESCRIPTION OF THE DRAWINGS

FIG. 4 is a side elevation view of an alternative expandable electrode structure usable in association with the system shown in FIG. 1, in which an open spline structure is used to expand the structure;

FIG. 5 is the expandable electrode shown in FIG. 4, in which a slidable sheath is used to collapse the structure;

FIG. 6 is a side elevation view of an alternative expandable electrode structure usable in association with the system shown in FIG. 1, in which an interwoven mesh structure is used to expand the structure;

FIG. 7 is the expandable electrode shown in FIG. 6, in which a slidable sheath is used to collapse the structure;

FIG. 8 is a side elevation view of an alternative expandable interwoven mesh electrode structure usable in association with the system shown in FIG. 1, in which an interior bladder is used to expand the structure;

FIG. 9 is a side elevation view of an alternative expandable foam electrode structure usable in association with the system shown in FIG. 1;

FIG. 10 is a side elevation view of an alternative expandable electrode structure usable in association with the system shown in FIG. 1, in which an electrically actuated spline structure is used to expand the structure;

FIG. 12 is a side elevation view of an expandable electrode structure usable in association with the system shown in FIG. 1, in which a steering mechanism proximal to the structure steers the structure at the end of a catheter tube;

FIG. 13 is a side elevation view of an expandable electrode structure usable in association with the system shown in FIG. 1, in which a steering mechanism within the structure steers the structure at the end of a catheter tube;

FIG. 14 is a side elevation view of an expandable electrode structure usable in association with the system shown in FIG. 1, in which an axially and radially movable stilette in the structure is used to alter the shape of the structure;

FIGS. 15A to 15E are plan views of an assembly process for manufacturing an expandable electrode structure using an inflation medium to expand the structure;

FIGS. 16A to 16D are plan views of an assembly process for manufacturing an expandable electrode structure using an interior spline structure to expand the structure;

FIG. 17 is a side elevation view of an expandable electrode structure usable in association with the system shown in FIG. 1, in which an electrically conductive shell is deposited on the distal end of the structure;

FIG. 18 is a side elevation view of an expandable electrode structure usable in association with the system shown in FIG. 1, in which an electrically conductive foil shell is positioned for attachment on the distal end of the structure;

FIG. 19 is an enlarged section view of the wall of an expandable electrode structure usable in association with the system shown in FIG. 1, in which an electrically conductive material is coextruded within the wall;

FIG. 20 is a top view of an expandable electrode structure having an exterior shell of electrically conductive material formed in a segmented bull's-eye pattern;

FIGS. 21 and 22 are, respectively, side and top views of an expandable electrode structure having an exterior shell of electrically conductive material formed in a segmented pattern of energy transmission zones circumferentially spaced about a preformed, foldable body, and including multiple temperature sensing elements;

FIGS. 23, 24A, and 24B are enlarged side views showing the deposition of electrically conductive material to establish fold lines on the exterior of an expandable electrode structure;

FIG. 25 is a top view of an expandable electrode structure showing the preferred regions for attaching signal wires to an electrically conductive shell deposited on the distal end of the structure;

FIG. 26 is a side view of an expandable electrode structure showing the preferred regions for attaching signal wires to an electrically conductive shell deposited in a circumferentially segmented pattern on the structure;

FIG. 27 is a top view of an expandable electrode structure showing the preferred regions for attaching signal wires to an electrically conductive shell deposited in a bull's-eye pattern on the structure;

FIG. 29A is an enlarged side view of the distal end of an expandable electrode structure usable in association with the system shown in FIG. 1, showing the attachment of an ablation energy signal wire to the electrically conductive shell using a mechanical fixture at the distal end of the structure;

FIG. 29B is an enlarged exploded side view, portions of which are in section, of the mechanical fixture shown in FIG. 29A;

FIGS. 30 and 31 are side section views showing the attachment of a signal wire to an electrically conductive shell, the signal wire being snaked through the wall of the structure either one (FIG. 30) or multiple times (FIG. 31);

FIG. 32 is an enlarged section view of the wall of an expandable electrode structure usable in association with the system shown in FIG. 1, showing the laminated structure of the wall and the attachment of an ablation energy signal wire to the electrically conductive shell using laser windowing techniques;

FIG. 33 is a side view, with portions broken away and in section, of an expandable electrode structure usable in association with the system shown in FIG. 1, showing the attachment of a temperature sensing element to a fixture at the distal end of the structure;

FIG. 34 is an enlarged side section view of the wall of an expandable electrode structure usable in association with the system shown in FIG. 1, showing ways of attaching temperature sensing elements inside and outside the wall;

FIG. 35 is an enlarged side section view of the wall of an expandable electrode structure usable in association with the system shown in FIG. 1, showing a laminated structure and the creation of temperature sensing thermocouples by laser windowing and deposition;

FIG. 36 is a top view of an expandable electrode structure showing the preferred regions for attaching temperature sensing elements with respect to an electrically conductive shell deposited on the distal end of the structure;

FIG. 37 is a side view of an expandable electrode structure showing the preferred regions for attaching temperature sensing elements with respect to an electrically conductive shell deposited in a circumferentially segmented pattern on the structure;

FIG. 38 is a top view of an expandable electrode structure showing the preferred regions for attaching temperature sensing elements with respect to an electrically conductive shell deposited in a bull's-eye pattern on the structure;

FIG. 39 is a side view of an expandable electrode structure showing a pattern of holes for cooling the edge regions of an electrically conductive shell deposited in a circumferentially segmented pattern on the structure, the pattern of holes also defining a fold line between the segments of the pattern;

FIGS. 40A and 40B are enlarged views of a hole formed in the structure shown in FIG. 39, showing that the hole defines a fold line;

FIG. 41A is a side sectional view of an expandable electrode structure usable in association with the system shown in FIG. 1, which is capacitively coupled to tissue;

FIG. 41B is a diagrammatic view showing the electrical path that ablation energy follows when the electrode shown in FIG. 40A is capacitively coupled to tissue;

FIG. 42A is an side sectional view of an alternative expandable electrode structure usable in association with the system shown in FIG. 1, which is capacitively coupled to tissue;

FIG. 42B is a diagrammatic view showing the electrical path that ablation energy follows when the electrode shown in FIG. 41A is capacitively coupled to tissue;

FIG. 44 is a side elevation view of an expandable electrode structure that embodies the features of the invention, used in association with pacing and sensing electrodes.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

I. Overview of a System With an Expandable-Collapsible Electrode Structure

Figure 1:
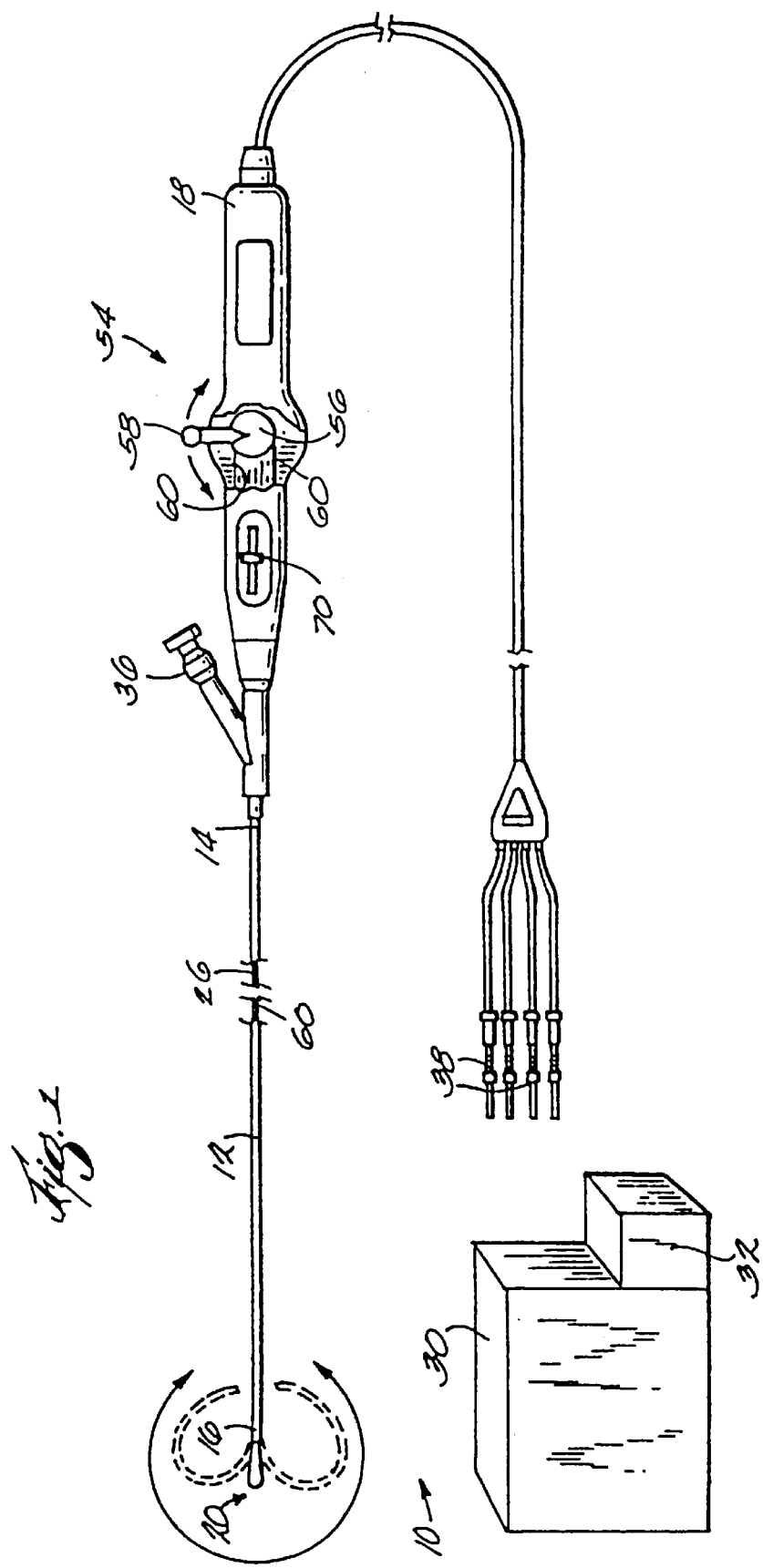
FIG. 1 is a plan view of a system for ablating heart tissue, which includes an expandable electrode structure that embodies the features of the invention.

FIG. 1 shows a tissue ablation system 10 that embodies the features of the invention.

The system 10 includes a flexible catheter tube 12 with a proximal end 14 and a distal end 16. The proximal end 14 carries a handle 18. The distal end 16 carries an electrode structure 20, which embodies features of the invention. The purpose of the electrode structure 20 is to transmit ablation energy.

As the embodiments of FIGS. 2 through 11 show in greater detail, the electrode structure 20 includes an expandable-collapsible wall forming a body 22. The geometry of the body 22 can be altered between an enlarged, or expanded, geometry having a first maximum diameter (depicted in various forms, for example, in FIGS. 2, 3, 4, 6, and 11A) and a collapsed geometry having a second maximum diameter less than the first maximum diameter (depicted in various forms, for example, in FIGS. 5, 7, 11B/C).

This characteristic allows the expandable-collapsible body 22 to assume a collapsed, low profile (ideally, less than 8 French diameter, i.e., less than about 0.267 cm) when introduced into the vasculature. Once located in the desired position, the expandable-collapsible body 22 can be urged into a significantly expanded geometry of, for example, approximately 7 to 20 mm.

The expanded geometry of the body 22, coupled with its inherent flexibility, significantly enhance the lesion creation characteristics of the electrode structure. Further details of the body and the ways to alter its geometry will be provided later.

All or a portion of the wall forming the body 22 carries an electrically conductive material that forms an electrode surface. As the embodiments of FIGS. 2 through 11 show in greater detail, the electrically conductive material comprises an electrically conductive shell 24 overlying all or a portion of the expandable-collapsible body 22. The shell 24 serves as the transmitter of energy that ablates body tissue. While the type of ablation energy used can vary, in the illustrated and preferred embodiment, the shell 24 serves to transmit radio frequency (RF) electromagnetic energy.

The shell 24 is flexible enough to adopt to the range of geometries, from collapsed to expanded, that the expandable-collapsible body 22 assumes. Still, the shell 24 preferably resists stretching within this range, to thereby minimize "thinning." Thinning of the shell 24 creates localized changes to the shell 24, with attendant increases in resistance and "hot spots." For this reason, the elasticity of the expandable-collapsible body 22 and shell 24 should be selected to fall within acceptable bounds so that the ability to fold is retained while preserving stability during inflation. Further details of the energy transmitting shell 24 will be provided later.

As will be shown in greater detail later (see FIGS. 25 to 32), the shell 24 is coupled to one or more signal wires 26. The signal wires 26 extend from the shell 24, through the catheter tube 12, to external connectors 28 on the handle 18 (see FIG. 1). The connectors 28 electrically couple the shell 24 to a radio frequency generator 30.

In the preferred and illustrated embodiment (see FIG. 1), a controller 32 is associated with the generator 30, either as an integrated unit or as a separate interface box. The controller 32 governs the delivery of radio frequency ablation energy to the shell 24 according to preestablished criteria. Further details of this aspect of the system 10 will be described later.

The system 10 as just described is suited for ablating myocardial tissue within the heart. In this environment, a physician moves the catheter tube 12 through a main vein or artery into a heart chamber, while the expandable-collapsible body 22 of the electrode structure 20 is in its low profile geometry. Once inside the desired heart chamber, the expandable-collapsible body 22 is enlarged into its expanded geometry, and the shell 24 is placed into contact with the targeted region of endocardial tissue. Radio frequency energy is conveyed from the generator 30 to the shell 24, as governed by the controller 32. The shell 24 transmits radio frequency energy into tissue to a return electrode, which is typically an external patch electrode (forming a unipolar arrangement). Alternatively, the transmitted energy can pass through tissue to an adjacent electrode in the heart chamber (forming a bipolar arrangement), or between segments in the shell 24, as will be described later (also forming a bipolar arrangement). The radio frequency energy heats the tissue forming a lesion.

The expanded geometry of the expandable-collapsible body 22 enhances the energy transmission characteristics of the structure 20. The structure 20, when expanded, is able to form tissue lesions that are significantly larger in terms of size and volume than the body's initial collapsed profile during introduction would otherwise provide.

It should also be appreciated that the expandable-collapsible electrode structure 20 as just described is also suited for mapping myocardial tissue within the heart. In this use, the shell 24 senses electrical activity in the heart. The sensed electrical activity is conveyed to an external monitor, which processes the potentials for analysis by the physician. The use of an expandable-collapsible electrode structure for this purpose is generally disclosed in Edwards et al. U.S. Pat. No. 5,293,869.

It should also be appreciated that the expandable-collapsible electrode structure 20 can be used alternatively, or in combination with sensing electrical activities, to convey pacing signals. In this way, the structure 20 can carry out pace mapping or entrainment mapping. The expanded electrode structure 20 can also be used to convey pacing signals to confirming contact with tissue before ablating. The ability to carry out pacing to sense tissue contact is unexpected, given that the expanded structure 20 presents a surface area significantly greater than that presented by a conventional 4 mm/8 F electrode.

As FIG. 44 shows, the catheter tube 20 can also carry one or more conventional ring electrodes 21 for bipolar sensing. A conventional pacing or unipolar sensing electrode 23 may also be provided, appended at the distal end of the structure 20.

II. The Expandable-Collapsible Body

The expandable-collapsible body 22 is made from a material selected to exhibit the following characteristics:

(i) the material must be capable, in use, of transition between an expanded geometry having a first maximum diameter and a collapsed geometry having a second maximum diameter less than the first diameter. In this respect, the material can be formed into an expandable-collapsible bladder or balloon body having an open interior. The body is flexible enough to assume the expanded geometry as a result of a normally open solid support structure within the interior, or the opening of a normally closed support structure within the interior, or the introduction of fluid pressure into the interior, or a combination of such interior forces. In this arrangement, the body is caused to assume the collapsed geometry by an exterior compression force against the normally open interior support structure, or the closing of the interior support structure, or the removal of the interior fluid pressure, or a combination of such offsetting forces. Alternatively, the material can be a preformed body with a memory urging it toward a normally expanded geometry. In this arrangement, the preformed body is caused to assume the collapsed geometry by the application of an external compression force. In this arrangement, the preformed body can have an open interior, or can comprise, for example, a collapsible composite foam structure.

(ii) the material must be biocompatible and able to withstand high temperature conditions, which arise during manufacture and use.

(iii) the material must possess sufficient strength to withstand, without rupture or tearing, external mechanical or fluid forces, which are applied to support and maintain its preformed geometry during use.

(iv) the material must lend itself to attachment to the catheter tube 12 through the use of straightforward and inexpensive adhesive, thermal, or mechanical attachment methods.

(v) the material must be compatible with the electrically conductive shell 24 to achieve secure adherence between the two.

Thermoplastic or elastomeric materials that can be made to meet these criteria include polyimide (kapton), polyester, silicone rubber, nylon, mylar, polyethelene, polyvinyl chloride, and composite structures using these and other materials.

The incidence of tissue sticking to the exterior of the body 22 during use can be mediated by the inclusion of low friction materials like PTFE. The propensity of the exterior of the body 22 to cause blood clotting and/or embolization can be reduced by incorporating non-thrombogenic material onto or into the exterior of the body 22.

Polyimide is particularly preferred for the expandable-collapsible body. Polyimide is flexible, but it is not elastic. It can withstand very high temperatures without deformation. Because polyimide is not elastic, it does not impose stretching forces to the shell, which could lead to electrical conductivity decreases, as above described.

The expandable-collapsible body 22 can be formed about the exterior of a glass mold. In this arrangement, the external dimensions of the mold match the desired expanded internal geometry of the expandable-collapsible body 22. The mold is dipped in a desired sequence into a solution of the body material until the desired wall thickness is achieved. The mold is then etched away, leaving the formed expandable-collapsible body 22.

Various specific geometries, of course, can be selected. The preferred geometry is essentially spherical and symmetric, with a distal spherical contour, as FIGS. 2 to 11 show in various forms. However, nonsymmetric geometries can be used. For example, the expandable-collapsible body 22 may be formed with a flattened distal contour, which gradually curves or necks inwardly for attachment with the catheter tube 12.

The expandable-collapsible body 22 may also be blow molded from an extruded tube. In this arrangement, the body 22 is sealed at one end using a mechanical clamp, adhesive, or thermal fusion. The opposite open end of the body 22 is left open. The sealed expandable-collapsible body 22 is placed inside the mold. An inflation medium, such as high pressure gas or liquid, is introduced through the open tube end. The mold is exposed to heat as the tube body 22 is inflated to assume the mold geometry. The formed expandable-collapsible body 22 is then pulled from the mold.

A. Expansion Using Interior Fluid Pressure

Figure 2:
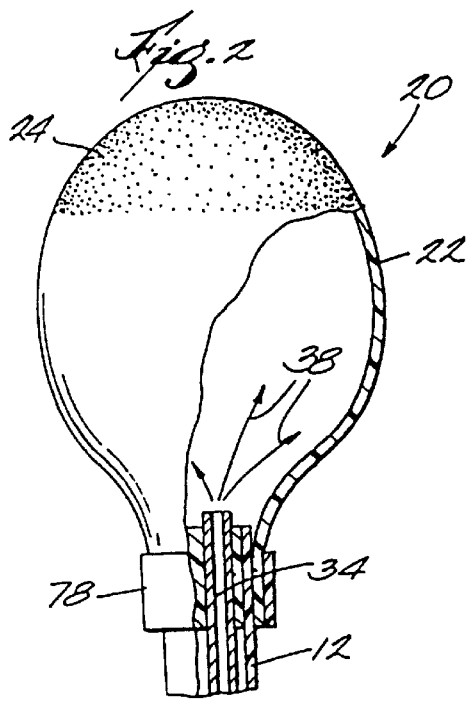
FIG. 2 is a side elevation view of an expandable electrode structure usable in association with the system shown in FIG. 1, in which an inflation medium is used to expand the structure.
Figure 3A:
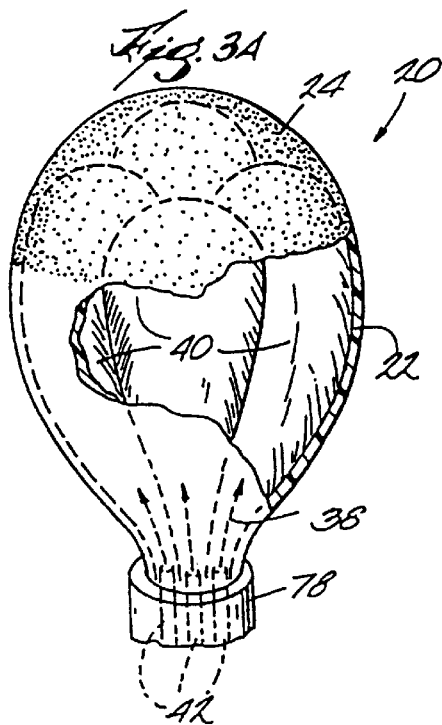
FIG. 3A is a side elevation view of an alternative expandable electrode structure usable in association with the system shown in FIG. 1, in which an inflation medium is used to expand separate multiple chambers within the structure.

In the embodiments shown in FIGS. 2 and 3A/B/C, fluid pressure is used to inflate and maintain the expandable-collapsible body 22 in the expanded geometry.

In this arrangement, the catheter tube 12 carries an interior lumen 34 along its length. The distal end of the lumen 34 opens into the hollow interior of the expandable-collapsible body 22, which has been formed in the manner just described. The proximal end of the lumen 34 communicates with a port 36 (see FIG. 1) on the handle 18.

An inflation fluid medium (arrows 38 in FIG. 2) is conveyed under positive pressure through the port 36 and into the lumen 34. The fluid medium 38 fills the interior of the expandable-collapsible body 22. The fluid medium 38 exerts interior pressure to urge the expandable-collapsible body 22 from its collapsed geometry to the enlarged geometry desired for ablation.

The inflating fluid medium 38 can vary. Preferably, it comprises a liquid such as water, saline solution, or other biocompatible fluid. Alternatively, the inflating fluid medium 38 can comprise a gaseous medium such as carbon dioxide or air.

Regardless of the type of fluid medium 38, the inflation preferably occurs under relatively low pressures of up to 30 psi. The pressure used depends upon the desired amount of inflation, the strength and material used for the body 22, and the degree of flexibility required, i.e., high pressure leads to a harder, less flexible body 22.

More than one fluid conveying lumen 34 may be used. The multiple lumens 34 can, for example, speed up the introduction or removal of the inflating medium 38 from the body 22. Multiple lumens can also serve to continuously or intermittently recycle the inflating medium 38 within the body 22 for controlling the temperature of the body, as will be described in greater detail later. Multiple lumens can also be used, with at least one of the lumens dedicated to venting air from the structure 20.

In an alternative embodiment shown in FIG. 3A, a group of sealed bladders compartmentalize the interior of the formed body into chambers 40. One or more lumens 42 passing through the catheter tube 12 convey the inflating gas or liquid medium 38 into each chamber 40, as described above. The inflated chambers 40 collectively hold the expandable-collapsible body 22 in its expanded condition. Removal of the inflation medium 38 deflates the chambers 40, collapsing the expandable-collapsible body 22.

The bladders defining the chambers 40 may be separately formed by molding in generally the same fashion as the main expandable-collapsible body 22. The bladder material need not have the same resistance to high temperature deformation as the expandable-collapsible body 22. If desired, the bladders may also be deposition coated with a thermal insulating material to thermally insulate them from the main expandable-collapsible body 22.

Figure 3B:
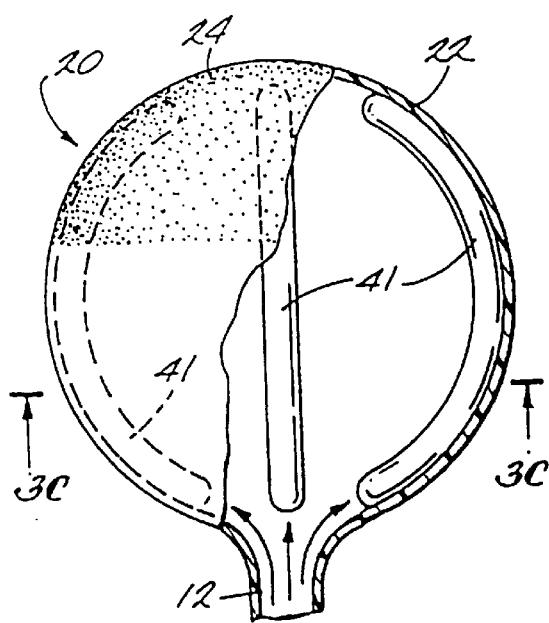
FIG. 3B is a side elevation view of an alternative expandable electrode structure usable in association with the system shown in FIG. 1, in which an inflation medium is used to expand integrally formed multiple chambers within the structure.
Figure 3C:
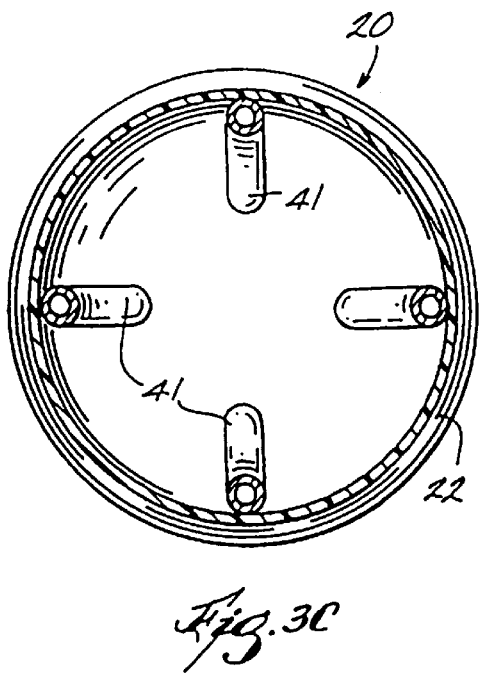
FIG. 3C is a top section view of the electrode structure shown in FIG. 3B, taken generally along line 3C—3C in FIG. 3B.

Alternatively, as FIGS. 3B and 3C show, the interior chambers 40 can take the form of tubular, circumferentially spaced ribs 41 attached to the interior of the body 22. In this arrangement, the ribs 41 preferably constitute integrally molded parts of the body 22.

As explained in connection with the FIG. 3A embodiment, a single lumen may service all chambers ribs 41. However, multiple lumens individually communicating with each rib 41 provide the ability to more particularly control the geometry of the expanded body 22, by selectively inflating some but not all the ribs 41 or chambers 40.

Figure 3E:
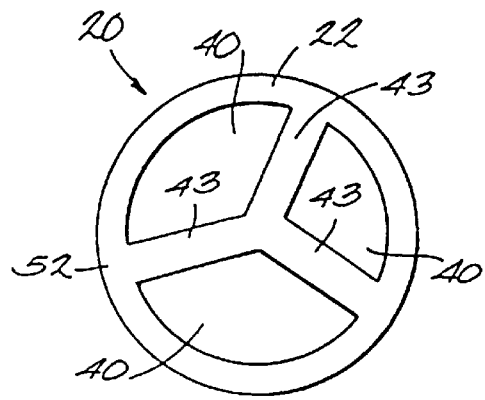
FIG. 3E is a top view of an alternative expandable-collapsible electrode structure with a body having interior coextruded webs that compartmentalize the body into multiple interior chambers.

As FIG. 3E shows, the body 22 may be extruded with interior webs 43. When the body is in its expanded geometry, the interior webs 43 compartmentalize the body 22 into the interior chambers 40, as already described. As before described, multiple lumens preferably individually communicate with each formed chamber 40 for conveying inflation medium and for venting air.

Figure 3D:
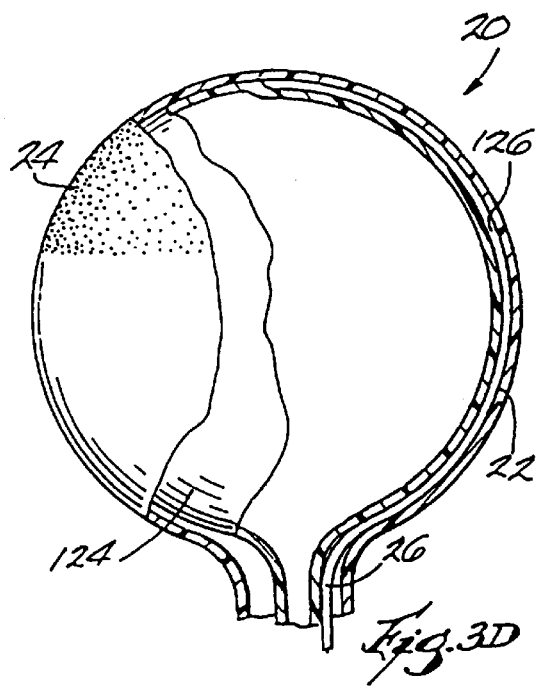
FIG. 3D is a side elevation view of an alternative expandable electrode structure usable in association with the system shown in FIG. 1, in which an inflation medium is used to expand a single chamber within the structure.

As FIG. 3D shows, a separate, single interior chamber 124 can be used instead of the compartmentalized chambers 40 or ribs 41 shown in FIGS. 3A, 3B, and 3C to receive the inflation medium for the exterior body 22. As will be described in greater detail later, this arrangement creates an intermediate region 126 between the interior of the body 22 and the exterior of the chamber 124, through which signal wires 26 can be passed for coupling to the shell 24.

B. Interior Support Structures

In the embodiments shown in FIGS. 4 to 7, collapsible, interior structures 44 sustain the expandable-collapsible body 22 in the expanded geometry. The presence of the interior support structure 44 eliminates the need to introduce air or liquid as an inflation medium 38. Possible difficulties of fluid handling and leakage are thereby avoided.

In the embodiment shown in FIGS. 4 and 5, the expandable-collapsible body 22 is held in its expanded geometry by an open interior structure 44 formed by an assemblage of flexible spline elements 46. The spline elements 46 are made from a resilient, inert wire, like nickel titanium (commercially available as Nitinol material), or from a resilient injection molded inert plastic or stainless steel. The spline elements 46 are preformed in a desired contour and assembled to form a three dimensional support skeleton, which fills the interior space of the expandable-collapsible body 22.

In this arrangement, the supported expandable-collapsible body 22 is brought to a collapsed geometry by outside compression applied by an outer sheath 48 (see FIG. 5), which slides along the catheter tube 12. As FIG. 5 shows, forward movement of the sheath 48 advances it over the expanded expandable-collapsible body 22. The sliding sheath 48 encompasses the expandable-collapsible body 22, compressing the interior spline elements 46 together. The expandable-collapsible body 22 collapses into its low profile geometry within the sheath 48.

Rearward movement of the sheath 48 (see FIG. 4) retracts it away from the expandable-collapsible body 22. Free from the confines of the sheath 48, the interior support structure 44 of spline elements 46 springs open into the three dimensional shape. The expandable-collapsible body 22 returns to its expanded geometry upon the spline elements 46.

In an alternative embodiment, as FIGS. 6 and 7 show, the expandable-collapsible body 22 is supported upon a closed, three dimensional structure 44 formed by a resilient mesh 50. The mesh structure 50 is made from interwoven resilient, inert wire or plastic filaments preformed to the desired expanded geometry. The mesh structure 50 provides interior support to hold the expandable-collapsible body 22 in its expanded geometry, in the same way as the open structure of spline elements 46 shown in FIG. 4.

As FIG. 7 further shows, a sliding sheath 48 (as previously described) can also be advanced along the catheter tube 12 to compress the mesh structure 50 to collapse mesh structure 50 and, with it, the expandable-collapsible body 22. Likewise, retraction of the sheath 48 removes the compression force (as FIG. 6 shows), and the freed mesh structure 50 springs open to return the expandable-collapsible body 22 back to its expanded geometry.

By interweaving the mesh filaments close enough together, the mesh structure 50 itself could serve as the support for the electrically conductive shell 24, without need for the intermediate expandable-collapsible body 22. Indeed, all or a portion of the mesh filaments could be made electrically conductive to themselves serve as transmitters of ablation energy. This arrangement of interwoven, electrically conductive filaments could supplement or take the place of the electrically conductive shell 24.

Alternatively, as FIG. 8 shows, the mesh structure 50 can be made to normally assume the collapsed geometry. In this arrangement, one or more interior bladders 126 can accommodate the introduction of an inflation medium to cause the mesh structure 50 to assume the expanded geometry.

If the mesh structure 50 is tightly woven enough to be essentially liquid impermeable, the interior bladder 126 could be eliminated. In this arrangement, the introduction of a biocompatible liquid, such as sterile saline, directly into the interior of the structure 50 would cause the structure to assume the expanded geometry.

FIG. 9 shows yet another alternative expandable-collapsible structure. In this embodiment, a foam body 128 molded to normally assume the shape of the expanded geometry forms the interior support structure for the body 22. As with the interior structures 44, the presence of the foam body 128 eliminates the need to introduce air or liquid as an inflation medium. Also like the interior structures 44, a sliding sheath (not shown but as previously described) can be advanced along the catheter tube 12 to compress the foam body 128 and overlying body 22 into the collapsed geometry. Likewise, retraction of the sheath removes the compression force. The foam body 128, free of the sheath, springs open to return the expandable-collapsible body 22 back to the expanded geometry. It should be appreciated that the foam body 128 can provide interior, normally expanded support to the mesh structure 50 in the same way.

As FIG. 10 shows, the geometry of the expandable-collapsible body 22 can be controlled electrically. This arrangement includes an assemblage of spline elements 132 within the body 22. The spline elements 132 are made of a material that undergoes shape or phase change in response to heating. Nickel titanium wire is a material having this characteristic. Alternatively, the spline elements 132 could comprise an assembly of two metals having different coefficients of expansion.

The body 22 overlies the spline elements 132. The spline elements 132 are coupled to an electrical current source 134. Current flow from the source 134 through the spline elements 132 resistively heats the elements 132. As a result, the spline elements 132 change shape.

As FIG. 10 shows, the spline elements 132 normally present the collapsed geometry. Current flow through the spline elements 132 causes expansion of the elements 132, thereby creating the expanded geometry (as shown by arrows and phantom lines in FIG. 10). It should be appreciated that the spline elements 132 could alternatively normally present the expanded geometry and be made to contract, thereby assuming the collapsed geometry, in response to current flow.

C. Folding

In all the representative embodiments, the expandable-collapsible body 22 can be molded with preformed regions 52 (see FIGS. 11A/B/C) of reduced thickness, forming creases. To create these crease regions 52, the mold has a preformed surface geometry such that the expandable-collapsible material would be formed slightly thinner, indented, or ribbed along the desired regions 52. Alternatively, the use of interior coextruded webs 43, as FIG. 3E shows, also serves to form the crease regions 52 along the area where the webs 43 contact the interior wall of the body 22.

Figure 11A:
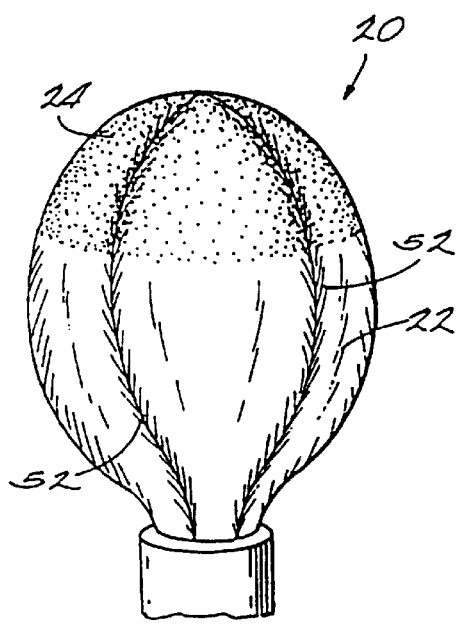
FIG. 11A is a side elevation view of an alternative expandable electrode structure usable in association with the system shown in FIG. 1, in which the electrode structure is pleated or creased to promote folding upon collapse.
Figure 11B:
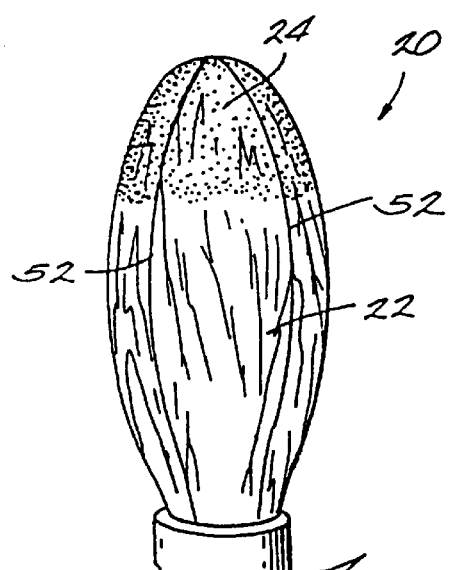
FIG. 11B is the electrode shown in FIG. 11A in the process of folding while collapsing.
Figure 11C:
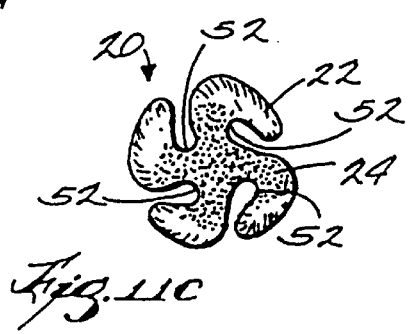
FIG. 11C is the electrode shown in FIG. 11A as folded upon collapse.
Figure 28A:
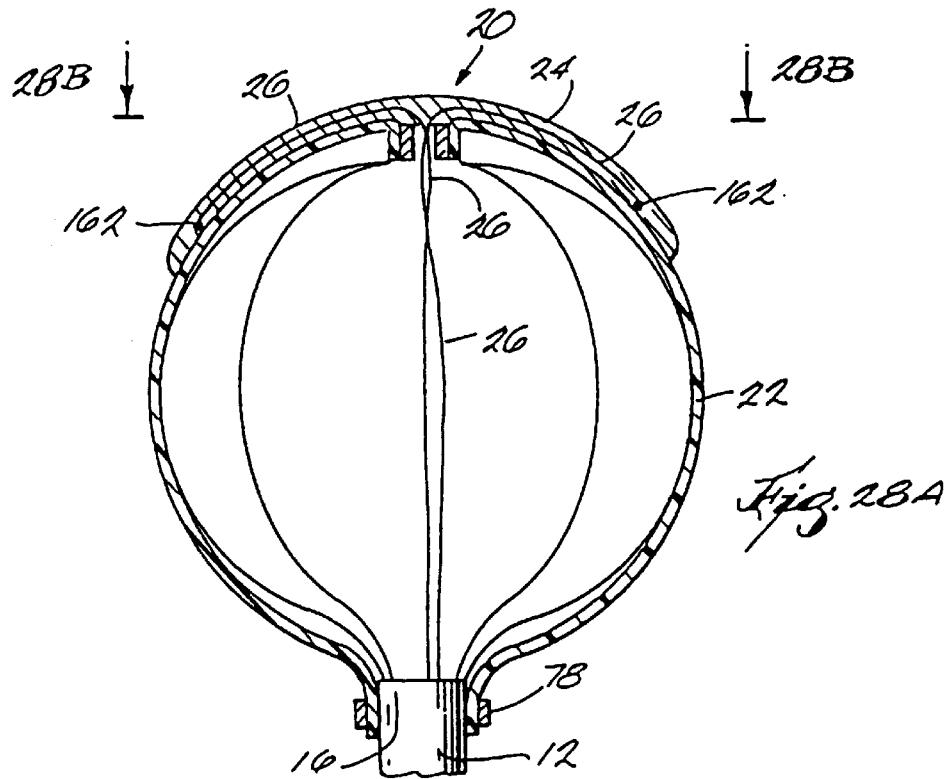
FIGS. 28A and 28B are, respectively side section and top views showing the attachment of signal walls to an electrically conductive shell deposited on the distal end of the structure, the signal wires being led through the distal end of the structure.
Figure 28B:
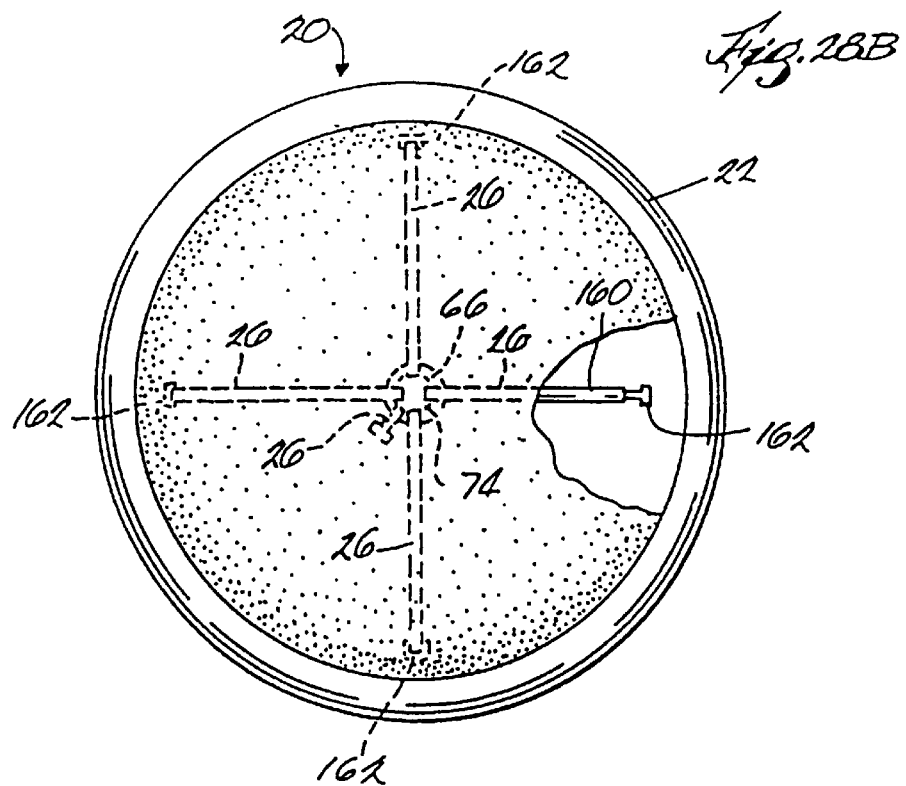

As FIGS. 11B/C show, the expandable-collapsible body 22 collapses about these regions 52, causing the body 22 to circumferentially fold upon itself in a consistent, uniform fashion. The resulting collapsed geometry can thus be made more uniform and compact.

In the embodiments where an inflation medium 38 applies positive pressure to expand the expandable-collapsible body 22, a negative fluid pressure can be applied inside the expandable-collapsible body 22 to draw the fold regions 52 further inward. In the embodiment where the interior structure 44 of open spline elements 46 supports the expandable-collapsible body 22, the fold regions 52 are preferably aligned in the spaces between the spline elements 46 to take best advantage of the prearranged folding action.

Alternative ways of creating fold regions 52 in the body 22 will be described in greater detail later.

D. Steering

In the illustrated and preferred embodiment, a distal steering mechanism 54 (see FIG. 1) enhances the manipulation of the electrode structure 20, both during and after deployment.

The steering mechanism 54 can vary. In the illustrated embodiment (see FIG. 1), the steering mechanism 54 includes a rotating cam wheel 56 coupled to an external steering lever 58 carried by the handle 18. The cam wheel 56 holds the proximal ends of right and left steering wires 60. The wires 60 pass with the ablation energy signal wires 26 through the catheter tube 12 and connect to the left and right sides of a resilient bendable wire or leaf spring 62 adjacent the distal tube end 16 (see FIG. 12). Further details of this and other types of steering mechanisms are shown in Lundquist and Thompson U.S. Pat. No. 5,254,088, which is incorporated into this Specification by reference.

In FIG. 12, the leaf spring 62 is carried within in the distal end 16 of the catheter tube 12, to which the electrode structure 20 is attached. As FIGS. 1 and 12 show, forward movement of the steering lever 58 pulls on one steering wire 60 to flex or curve the leaf spring 62, and, with it, the distal catheter end 16 and the electrode structure 20, in one direction. Rearward movement of the steering lever 58 pulls on the other steering wire 60 to flex or curve the leaf spring 62, and, with it, the distal catheter end 16 and the electrode structure 20, in the opposite direction.

In FIG. 13, the leaf spring 62 is part of a distal fixture 66 carried within the electrode structure 20 itself. In this arrangement, the leaf spring 62 extends beyond the distal catheter end 16 within a tube 64 inside the expandable-collapsible body 22. The distal end of the leaf spring 62 is secured to a distal fixture 66. The distal fixture 66 is itself attached to the distal end of the body 22. Further details of attaching the fixture 66 to the distal end of the body 22 will be described in greater detail later.

As FIG. 13 shows, forward movement of the steering lever 58 bends the leaf spring 62 in one direction within the expandable-collapsible body 22, deflecting the distal fixture 66 with it. This deforms the expandable-collapsible body 22 in the direction that the leaf spring 62 bends. Rearward movement of the steering lever 58 bends the leaf spring 62 in the opposite direction, having the opposite deformation effect upon the expandable-collapsible body 22.

In either arrangement, the steering mechanism 54 is usable whether the expandable-collapsible body is in its collapsed geometry or in its expanded geometry.

E. Push-Pull Stilette

In FIG. 14, a stilette 76 is attached to the distal fixture 66. The stilette extends inside the body 22, through the catheter tube 12, to a suitable push-pull controller 70 on the handle 18 (see FIG. 1). The stilette 76 is movable along the axis of the catheter tube 12. Moving the stilette 76 forward pushes axially upon the distal fixture 66. Moving the stilette 76 rearward pulls axially upon the distal fixture 66. The geometry of the body 22 elongates or expands accordingly.

The stilette 76 can be used in association with an expandable-collapsible body 22 that is expanded by an inflation medium 38. In this arrangement, when the expandable-collapsible body 22 is collapsed, forward movement of the stilette 76, extends the distal fixture 66 to further urge the expandable-collapsible body 22 into a smaller diameter profile for introduction.

When used in association with an expandable-collapsible body 22 that is internally supported by the spline structure 46 or the mesh structure 50, the stilette 76 can be used instead of the slidable outer sheath 48 to expand and collapse the expandable-collapsible body 22. Pushing forward upon the stilette 76 extends the spline structure 46 or mesh structure 50 to collapse the expandable-collapsible body 22. Pulling rearward upon the stilette 76, or merely releasing the pushing force, has the opposite effect, allowing the spline structure 46 or mesh structure 50 to assume its expanded geometry.

When used with either inflated or mechanically expanded expandable-collapsible bodies 22, pulling rearward upon the stilette 76 also has the effect of altering the expanded geometry by flattening the distal region of the expandable-collapsible body 22.

While the stilette 76 can be used by itself, in the illustrated embodiment (see FIG. 14), the distal end of the stilette 76 near the fixture 66 comprises the bendable leaf spring 62, thereby providing a radial steering function in tandem with the axial push-pull action of the stilette 76.

There are various ways to combine the steering mechanism 54 with the stilette 76. In the illustrated embodiment, a collar 136 is retained by a heat-shrink fit within tubing 64. The collar 136 has a central aperture 138 through which a leaf spring 62 at the end of the stilette 76 passes for movement along the axis of the catheter tube 12. Steering wires 60 are attached to the collar 136. Pulling on the steering wires 60 radially deflects the collar 136, thereby bending the leaf spring 62 at the end of the stilette 76 in the direction of the pulled steering wire 60.

F. Attachment to Catheter Tube

A sleeve 78 (see, e.g., FIG. 2) couples the near end of the expandable-collapsible body 22 to the distal end 16 of the catheter tube. The sleeve 78 withstands the forces exerted to expand the expandable-collapsible body 22, resisting separation of the body 22 from the catheter tube 12. In FIG. 2, where an inflation medium 38 is used, the sleeve 78 also forms a fluid seal that resists leakage of the medium at inflation pressures.

The sleeve 78 can be secured about the catheter tube in various ways, including adhesive bonding, thermal bonding, mechanical bonding, screws, winding, or a combination of any of these.

FIGS. 15A to 15E show the details of a preferred assembly process for an expandable-collapsible body 22 whose geometry is altered by use of fluid pressure, such as previously shown in FIGS. 2 and 3. The body 22 is extruded as a tube 140 having an extruded interior diameter, designated $ID_1$ (see FIG. 15A). The extruded interior diameter $ID_1$ is selected to be less than the exterior diameter of the distal stem 142 of the catheter tube 12 to which the body 22 will ultimately be attached.

As FIG. 15D shows, the stem 142 comprises an elongated, stepped-down tubular appendage, which extends beyond the distal end 16 of the catheter tube 12. The distal end of the stem 142 is sealed. The exterior diameter of the stem 142 is designated in FIG. 15D as $ED_S$. The stem 142 includes a central lumen 152 for carrying inflation medium. Spaced apart holes 154 on the stem 142 communicate with the lumen to convey the inflation medium into the body 22, when attached to the stem 142.

As FIG. 15A shows, the material of the extruded tube 140 is preferably cross linked by exposure to gamma radiation 168 or an equivalent conventional treatment. The cross linking enhances the capability of the material of the tube 140 to recover its shape after mechanical deformation.

After cross linking, the extruded tube 140 is mechanically deformed by heat molding into the body 22 having the desired collapsed geometry, in a manner previously described. The body geometry (see FIG. 15B) includes proximal and distal neck regions 144 and 146 and an intermediate main body region 148. The neck regions 144 and 146 have an enlarged interior diameter (designated $ID_2$ in FIG. 15B) that is slightly greater than catheter stem diameter $ED_S$, to permit a slip fit of the body 22 over the stem 142. The intermediate main body region 148 has an enlarged exterior diameter selected for the collapsed geometry of the body 22. To preserve the desired wall thickness, the enlarged exterior diameter of the tube 140 should be about twice the original extruded outer diameter of the tube 140.

As FIG. 15C shows, the tubing ends 150 extending beyond the neck regions 144 and 146 are cut away. As FIG. 15D shows, the body 22 is slip fitted over the stem 142. Heat is applied to shrink fit the neck regions 144 and 146 about the stem 142 (see FIG. 15E). Due to molding, the memory of these regions 144 and 146, when heated, seek the original interior diameter $ID_1$ of the tubing 140, thereby proving a secure interference fit about the stem 142.

Preferably, after forming the interference fit between the neck regions 144 and 146 and the stem 142, additional heat is provided to thermally fuse the regions 144 and 146 to the stem 142. Last, the sleeve 78 is heat-shrunk in place about the proximal neck region 144 (see FIG. 15E). The sleeve 78 can comprise a heat-shrink plastic material or phase changeable metal material, like nickel titanium. Alternatively, the sleeve 78 can be heat-shrunk into place without an intermediate thermal fusing step.

FIGS. 16A to 16D show the details of a preferred assembly process for an expandable-collapsible body 22 whose geometry is altered by use of an interior support structure 44 of spline elements 46, such as previously shown in FIGS. 4 and 5. After heat molding the body 22 in the manner shown in FIGS. 15A to 15C, the distal neck region 146 is secured by heat shrinking about the distal fixture 66 (see FIG. 16A). As FIG. 16A shows, the distal fixture 66 has, preattached to it, the distal end of the spline element structure 44, as well as any desired steering mechanism 54, stilette 76, or combination thereof (not shown in FIGS. 16A to 16D). When initially secured to the fixture 66, the main region 148 of the body 22 is oriented in a direction opposite to the spline element structure 44.

After securing the distal neck region 146 to the fixture 66, as just described, the body 22 is everted about the distal fixture 66 over the spline element structure 44 (see FIG. 16B). The proximal end of the spline element structure 44 is secured to an anchor 156 carried by the distal catheter end 16 (see FIG. 16C), and the everted proximal neck region 144 is then slip fitted over the catheter stem 158. As FIG. 16C shows, the catheter stem 158 in this arrangement does not extend beyond the neck region 144 of the body 22.

Heat is then applied to shrink fit the neck region 144 about the stem 158 (see FIG. 16D). Preferably, after forming this interference fit between the neck region 144 and the stem 158, additional heat is provided to thermally fuse the region 144 to the stem 158. Last, the sleeve 78 is heat-shrunk in place about the proximal neck region 144. Alternatively, the sleeve 78 can be heat-shrunk into place without an intermediate thermal fusing step.

III. The Electrically Conducting Shell

The purpose of the electrically conducting shell 24 is to transmit ablation energy, which in the illustrated and preferred embodiment comprises electromagnetic radio frequency energy with a frequency below about 1.0 GHz. This type of ablating energy heats tissue, mostly ohmically, to form lesions without electrically stimulating it. In this arrangement, the shell 24 should possess the characteristics of both high electrical conductivity and high thermal conductivity. It should also be appreciated that the shell 24 could form an antenna for the transmission of higher frequency microwave energy.

By altering the size, location, and pattern of the shell 24, along with adjusting the power level and time that the radio frequency ablation energy is transmitted, the electrode structure 20 is able to create lesions of different size and geometries.

A. Shell Geometry (Thermal Convective Cooling)

In one application, the shell creates lesion patterns greater than about 1.5 cm deep and/or about 2.0 cm wide. These lesion patterns are significantly deeper and wider than those created by conventional 8 F diameter/4 mm long electrodes, which are approximately 0.5 cm deep and 10 mm wide. The deeper and wider lesion patterns that the shell 24 can provide are able to destroy epicardial and intramural ventricular tachycardia (VT) substrates.

As the following Example shows, the size and location of the shell 24 on the expandable-collapsible body 22, when expanded, significantly affects the size and geometry of the lesions formed by transmitting radio frequency ablation energy.

EXAMPLE 1

Finite element analysis was performed for a flexible, expanded electrode structure 20 having a 1.4 cm diameter and a wall thickness of approximately 200 $\mu$m. The model assumed a 100 $\mu$m thick coating of gold over the distal hemisphere of the structure 20, forming the electrically conductive shell 24. The constraint for the model was a lower limit on thickness and therefore the thermal conductivity of the shell 24.

For the model, the percent of electrically conductive shell 24 in contact with myocardial tissue, with the balance exposed to blood, was changed from 5%, 20%, 41%, and 100% tissue contact. Time and power of energy transmission were also varied. Power was changed to keep the maximum temperature of tissue under the shell 24 at 90° C. Maximum lesion depth, width, and volume were measured.

The following Table 1 presents the results:

TABLE 1

LESION GEOMETRY AS A FUNCTION OF TISSUE vs. BLOOD CONTACT WITH THE ELECTRICALLY CONDUCTIVE SHELL

| % Tissue Contact | Temp. (°C.) | Voltage (Volts) | Current (Amps) | Power (Watts) | Lesion Depth (cm) | Lesion Width (cm) | Lesion Volume (cm$^3$) |
|---|---|---|---|---|---|---|---|
| <5% | 92.1 | 84 | 1.67 | 140 | 2.1 | 5.4 | 36 |
| 20% | 89.7 | 81 | 1.55 | 125 | 2.5 | 4.9 | 41 |

TABLE 1-continued

LESION GEOMETRY AS A FUNCTION OF TISSUE vs. BLOOD CONTACT WITH THE ELECTRICALLY CONDUCTIVE SHELL

| % Tissue Contact | Temp. (°C.) | Voltage (Volts) | Current (Amps) | Power (Watts) | Lesion Depth (cm) | Lesion Width (cm) | Lesion Volume (cm$^3$) |
|---|---|---|---|---|---|---|---|
| 41% | 89.6 | 77 | 1.4 | 107 | 2.3 | 3.5 | 17 |
| 100% | 92.3 | 61 | 0.92 | 56 | 1.4 | 2.6 | 7 |

The lesions created in the above Table 1 are capable of making transmural lesions in the left ventricle and can therefore ablate epicardial VT substrates. The Table 1 shows that lesion size increases with an electrically conductive shell 24 presenting less percentage contact with tissue than blood. The shell presenting 100% contact with tissue (and none with blood), compared to the shell 24 presenting up to 41% percent of its surface to tissue had lower lesion depths.

With less relative contact with tissue than blood, the shell 24 is more exposed to the blood pool and its convective cooling effect. The blood cools the shell 24 it contacts. Heat is lost from tissue under the shell 24 into the blood pool. This emulation of active cooling of the shell 24 causes more power to be transmitted to the tissue before maximum tissue temperatures are achieved, thereby creating larger lesions.

Table 1 highlights the importance of relatively high thermal conductivity for the shell 24, which can be achieved by material selection and controlling thickness. Given the same percentage contact with tissue versus blood, a higher thermal conductivity results in a higher cooling effect and a corresponding increase in lesion size.

The above Table 1 demonstrates the ability of the structure 20 carrying the shell 24 to transmit the proper amount of radio frequency energy to create large and deep lesions.

Additional tests were performed using shells 24 with a desirable lower percentage contact with tissue relative to blood (less than 50%). These tests varied the time of ablation energy transmission to gauge the effect upon lesion size.

The following Table 2 presents the results:

TABLE 2

LESION GEOMETRY AS A FUNCTION OF TIME OF ABLATION ENERGY TRANSMISSION, GIVEN THE SAME TISSUE vs. BLOOD CONTACT WITH THE ELECTRICALLY CONDUCTIVE SHELL

| % Tissue Contact | Power (Watts) | Time (Sec.) | Lesion Depth (cm) | Lesion Width (cm) |
|---|---|---|---|---|
| 5% | 110 | 25 | 0.5 | 1.6 |
| 5% | 110 | 60 | 1.2 | 2.4 |
| 41% | 67 | 25 | 0.35 | 1.4 |
| 41% | 67 | 60 | 0.9 | 2.0 |

The above Table 2 demonstrates the ability of the structure carrying the shell 24 to transmit the proper amount of radio frequency energy to create wide and shallow lesions. The effect is achieved by controlling both the delivered radio frequency power and the time of radio frequency energy application. Wide and shallow lesion patterns are effective in the treatment of some endocardially located substrates and atrial fibrillation substrates.

Tables 1 and 2 demonstrate the capability of the same expandable-collapsible electrode structure 20 with the desirable lower percentage contact with tissue relative to blood (less than 50%) to ablate epicardial, intramural, or endocardial substrates with a range of lesion patterns from wide and shallow to large and deep.

B. Surface Deposition of Shell

The electrically conductive shell 24 may be deposited upon the exterior of the formed expandable-collapsible body 22.

In this embodiment, a mask is placed upon the surface of the expandable-collapsible body 22 that is to be free of the shell 24. Preferably, as generally shown in FIG. 17, the shell 24 is not deposited on at least the proximal ⅓rd surface of the expandable-collapsible body 22. This requires that at least the proximal ⅓rd surface of the expandable-collapsible body 22 be masked, so that no electrically conductive material is deposited there.

The masking of the at least proximal ⅓rd surface of the expandable-collapsible body 22 is desirable for several reasons. This region is not normally in contact with tissue, so the presence of electrically conductive material serves no purpose. Furthermore, this region also presents the smallest diameter. If electrically conductive, this region would possess the greatest current density, which is not desirable. Masking the proximal region of smallest diameter, which is usually free of tissue contact, assures that the maximum current density will be distributed at or near the distal region of the expandable-collapsible body 22, which will be in tissue contact. The presence of the steering mechanism 54, already described, also aids in placing the shell-carrying distal tip in tissue contact.

The shell 24 comprises a material having a relatively high electrical conductivity, as well as a relative high thermal conductivity. Materials possessing these characteristics include gold, platinum, platinum/iridium, among others. These materials are preferably deposited upon the unmasked, distal region of the expandable-collapsible body 22. Usable deposition processes include sputtering, vapor deposition, ion beam deposition, electroplating over a deposited seed layer, or a combination of these processes.

Preferably (see FIG. 17), to enhance adherence between the expandable-collapsible body 22 and the shell 24, an undercoating 80 is first deposited on the unmasked distal region before depositing the shell 24. Materials well suited for the undercoating 80 include titanium, iridium, and nickel, or combinations or alloys thereof.

The total thickness of the shell 24 deposition, including the undercoating 80, can vary. Increasing the thickness increases the current-carrying and thermal conductive capacity of the shell 24. However, increasing the thickness also increases the potential of shell cracking or peeling during enlargement or collapse of the underlying expandable-collapsible body 22.

In a preferred embodiment, the deposition of the electrically conductive shell material should normally have a thickness of between about 5 μm and about 50 μm. The deposition of the adherence undercoating 80 should normally have a thickness of about 1 μm to about 5 μm.

C. Foil Shell Surface

In an alternative embodiment (see FIG. 18), the shell 24 comprises a thin sheet or foil 82 of electrically conductive metal affixed to the wall of the expandable-collapsible body 22. Materials suitable for the foil include platinum, platinum/iridium, stainless steel, gold, or combinations or alloys of these materials. The foil 82 is shaped into a predetermined geometry matching the geometry of the expandable-collapsible body 22, when expanded, where the foil 82 is to be affixed. The geometry of the metal foil 82 can be accomplished using cold forming or deep drawing techniques. The foil 82 preferably has a thickness of less than about 0.005 cm (50 μm). The foil 82 is affixed to the expandable-collapsible body 22 using an electrically insulating epoxy, adhesive, or the like.

The shell 24 of foil 82 offers advantages over the deposited shell 24. For example, adherence of the shell foil 82 upon the expandable-collapsible body 22 can be achieved without using the deposited undercoating 80. The shell foil 82 also aids in the direct connection of ablation energy wires 26, without the use of additional connection pads and the like, as will be described in greater detail later. The shell foil 82 also offers greater resistance to stretching and cracking in response to expansion and collapse of the underlying expandable-collapsible body 22. This offers greater control over resistance levels along the ablation energy transmitting surface.

D. Co-Extruded Electrically Conductive Shell

In an alternative embodiment (see FIG. 19), all or a portion of the expandable-collapsible wall forming the body 22 is extruded with an electrically conductive material 84. Materials 84 suitable for coextrusion with the expandable-collapsible body 22 include carbon black and chopped carbon fiber. In this arrangement, the coextruded expandable-collapsible body 22 is itself electrically conductive. An additional shell 24 of electrically conductive material can be electrically coupled to the coextruded body 22, to obtain the desired electrical and thermal conductive characteristics. The extra external shell 24 can be eliminated, if the coextruded body 22 itself possesses the desired electrical and thermal conductive characteristics.

The integral electrically conducting material 84 coextruded into the body 22 offers certain advantages over the external deposited shell 24 (FIG. 17) or shell foil 82 (FIG. 18). Coextrusion avoids the necessity of adherence between the shell 24 and the expandable-collapsible body 22. A body 22 coextruded with electrically conducting material 84 also permits more direct connection of ablation energy wires 34, without the use of additional connection pads and the like. The integrated nature of the coextruded material 84 in the body 22 protects against cracking of the ablation energy transmitting surface during expansion and collapse of the expandable-collapsible body 22.

The integral electrically conducting material 84 coextruded into the body 22 also permits the creation of a family of electrode structures 20, with the structures 20 differing in the amount of conductive material 84 coextruded into the wall of the respective body 22. The amount of electrically conductive material coextruded into a given body 22 affects the electrical conductivity, and thus the electrical resistivity of the body 22, which varies inversely with conductivity. Addition of more electrically conductive material increases electrical conductivity of the body 22, thereby reducing electrical resistivity of the body 22, and vice versa. It is thereby possible to specify among the family of structures 20 having electrically conductive bodies 22, the use of a given structure 20 according to a function that correlates desired lesion characteristics with the electrical resistivity values of the associated body 22.

EXAMPLE 2

A three-dimensional finite element model was created for an electrode structure having a body with an elongated shape, with a total length of 28.4 mm, a diameter of 6.4 mm, and a body wall thickness of 0.1 mm. The body of the structure was modeled as an electric conductor. Firm contact with cardiac tissue was assumed along the entire length of the electrode body lying in a plane beneath the electrode. Contact with blood was assumed along the entire length of the electrode body lying in a plane above the electrode. The blood and tissue regions had resistivities of 150 and 500 ohm·cm, respectively.

Analyses were made based upon resistivities of 1.2 k-ohm·cm and 12 k-ohm·cm for the electrode body.

Table 3 shows the depth of the maximum tissue temperature when RF ablation power is applied to the electrode at various power levels and at various levels of resistivity for the body of the electrode.

TABLE 3

| Resistivity of the Body (k-ohm · cm) | Power (Watts) | Time (Sec) | Maximum Tissue Temperature (°C.) | Depth of Maximum Tissue Temperature (cm) |
|---|---|---|---|---|
| 1.2 | 58 | 120 | 96.9 | 1.1 |
| 1.2 | 58 | 240 | 97.9 | 1.4 |
| 12 | 40 | 120 | 94.4 | 0.8 |
| 12 | 40 | 240 | 95.0 | 1.0 |

The electrode body with higher resistivity body was observed to generate more uniform temperature profiles, compared to a electrode body having the lower resistivity value. Due to additional heating generated at the tissue-electrode body interface with increased electrode body resistivity, less power was required to reach the same maximal temperature. The consequence was that the lesion depth decreased.

Therefore, by specifying resistivity of the body 22, the physician can significantly influence lesion geometry. The use of a low-resistivity body 22 results in deeper lesions, and vice versa. The following Table 4, based upon empirical data, demonstrates the relationship between body resistivity and lesion depths.

TABLE 4

| Resistivity (ohm · cm) | Power (Watts) | Temperature (°C.) | Lesion Depth (cm) | Time (sec) |
|---|---|---|---|---|
| 850 | 94 | 97 | 1.2 | 120 |
| 1200 | 58 | 97 | 1.1 | 120 |
| 12,000 | 40 | 95 | 0.8 | 120 |

E. Shell Patterns

When it is expected that ablation will occur with the distal region of body 22 oriented in end-on contact with tissue, the shell 24 should, of course, be oriented about the distal tip of the expandable-collapsible body 22. For this end-on orientation, the shell 24 may comprise a continuous cap deposited upon the distal ⅓rd to ½ of the body 22, as FIG. 17 shows. However, when distal contact with tissue is contemplated, the preferred embodiment (see FIG. 20) segments the electrically conductive shell 24 into separate energy transmission zones 122 arranged in a concentric "bull's-eye" pattern about the distal tip of the body 22.

The concentric bull's-eye zones 122 are formed by masking axially spaced bands on the distal region of the body 22, to thereby segment the deposit of the electrically conductive shell 24 into the concentric zones 122. Alternatively, preformed foil shells 82 can be applied in axially spaced bands on the distal region to form the segmented energy transmitting zones 122.

When it is expected that ablation will occur with the side region of the body 22 oriented in contact with tissue, the shell 24 is preferably segmented into axially elongated energy transmission zones 122, which are circumferentially spaced about the distal ⅓rd to ½ of the body 22 (see FIGS. 21 and 22).

The circumferentially spaced zones 122 are formed by masking circumferentially spaced areas of the distal region of the body 22, to thereby segment the deposit of the electrically conductive shell 24 into the zones 122. Alternatively, preformed foil shells 82 can be applied in circumferentially spaced-apart relationship on the distal region to form the segmented energy transmitting zones 122. Still alternatively, the circumferentially segmented energy transmission zones 122 may take the form of semi-rigid pads carried by the expandable-collapsible body 22. Adjacent pads overlap each other when the body 22 is in its collapsed geometry. As the body 22 assumes its expanded geometry, the pads spread apart in a circumferential pattern on the body 22.

Preferably, regardless of the orientation of the zones 122 (bull's-eye or circumferential), each energy transmission zone 122 is coupled to a dedicated signal wire 26 or a dedicated set of signal wires 26. This will be described later in greater detail. In this arrangement, the controller 32 can direct ablation energy differently to each zone 122 according to prescribed criteria, as will also be described in greater detail later.

The above describes the placement of a shell 24 on the exterior of the body 22. It should be appreciated that electrically conductive material can be deposited or otherwise affixed to the interior of the body 22. For example (as FIG. 44 shows), the interior surface of the body 22 can carry electrodes 402 suitable for unipolar or bipolar sensing or pacing. Different electrode placements can be used for unipolar or bipolar sensing or pacing. For example, pairs of 2-mm length and 1-mm width electrodes 402 can be deposited on the interior surface of the body 22. Connection wires 404 can be attached to these electrodes 100. Preferably the interelectrode distance is about 1 mm to insure good quality bipolar electrograms. Preferred placements of these interior electrodes are at the distal tip and center of the body 22. Also, when multiple zones are used, it is desired to have the electrodes 402 placed in between the ablation regions.

It is also preferred to deposit opaque markers 406 on the interior surface of the body 22 so that the physician can guide the device under fluoroscopy to the targeted site. Any high-atomic weight material is suitable for this purpose. For example, platinum or platinum-iridium can. can be used to build the markers 406. Preferred placements of these markers 406 are at the distal tip and center of the structure 22.

F. Folding Segmented Shells

As FIGS. 21 and 22 show, segmented energy transmitting zones 122 are well suited for use in association with folding expandable-collapsible bodies 22, as previously described in connection with FIGS. 11A/B/C. In this arrangement, the regions that are masked before deposition of the electrical conductive shell comprise the folding regions 52. In this way, the regions 52 of the expandable-collapsible body 22 that are subject to folding and collapse are those that do not carry an electrically conductive shell 24. The electrically conductive shell 24 is thereby protected against folding and stretching forces, which would cause creasing and current interruptions, or increases in resistance, thereby affecting local current densities and temperature conditions.

The selective deposition of the shell 24 in segmented patterns can itself establish predefined fold lines 52 on the body 22, without special molding of preformed regions of the body 22 (as FIGS. 11A/B/C contemplate). As FIGS. 23, 24A and 24B show, by controlling the parameters by which the shell segments 122 are deposited, predefined fold lines 52 can be created at the borders between the shell segments 122. These fold lines 52 are created due to the difference in thickness between adjacent regions which are coated with the shell 24 and those which are not.

More particularly, as FIGS. 23, 24A and 24B show, the region between segmented shell coatings will establish a fold line 52, when the distance between the coatings (designated x in FIGS. 24A and B) is greater than or equal to twice the thickness of the adjacent shell coatings 122 (designated t in FIGS. 24A and B) divided by the tangent of one half the minimum selected fold angle (designated $\alpha_{MIN}$ in FIG. 24A). This fold line relationship is mathematically expressed as follows:

$$x \geq \frac{2t}{\tan \alpha_{MIN}}$$

The minimum selected fold angle $2\alpha_{MIN}$ can vary according to the profile of the body 22 desired when in the collapsed geometry. Preferably, the minimum fold angle $2\alpha_{MIN}$ is in the range of 1° to 5°.

In this arrangement (see FIG. 23), the fold lines 52 created by controlled deposition of shell segments lie uniformly along (i.e., parallel to) the long axis of the body 22 (designated 170 in FIG. 23).

The uncoated fold lines 52 created at the borders between the thicker coated shell segments 122 can also be characterized in terms of relative electrical resistivity values. The coated segments 122 of electrically conductive material possess higher electrical conductivity than the uncoated fold lines 52. The resistivity of the fold lines 52, which varies inversely with conductivity, is thereby higher than the resistivity of the segments 122. To achieve the desired folding effect due to differential coating, the region in which folding occurs should have a resistivity that is greater than about ten times the resistivity of the segments 122 carrying electrically conductive material.

IV. Electrical Connection to Shell

It is necessary to electrically connect the shell 24 (or other ablation energy transmitting material 84) to the radio frequency energy generator 30 using the one or more signal wires 26. As before described, these signal wires 26, electrically connected to the shell 24, extend between the body 22 and the external connectors 28 through the catheter tube 12.

The connection between the signal wires 26 and the shell 24, whether deposited, foil layered, or coextruded, must remain intact and free of open circuits as the expandable-collapsible body 22 and shell 24 change geometries.

The electrical connection is preferably oriented proximate to the geometric center of the pattern that the associated ablation zone 122 defines. As FIGS. 25 to 27 show, the geometric center (designated GC) varies depending upon whether the zone 122 comprises a cap pattern (as FIG. 25 shows), or a circumferential segment pattern (as FIG. 26 shows), or a circumferential band or bull's-eye pattern (as FIG. 27 shows). At least one electrical connection should be present proximate to the respective geometric center of the pattern. This ensures that maximum current density is distributed about the geometric center of the zone and that similar current densities are distributed at the edges of the pattern.

Regardless of the shape of the pattern, additional electrical connections are preferably made in each ablation zone. In the case of a cap pattern or a segment pattern, the additional electrical connections (designated AC in, respectively, FIGS. 25 and 26) are distributed uniformly about the geometric center. In the case of a circumferential band of a bull's-eye pattern, the additional electrical connections (designated ACG in FIG. 27) are distributed uniformly along the arc along which the geometric center of the band lies.

Multiple electrical connections, at least one of which occurs proximate to the geometric center, provide more uniform current density distribution in the zone. These multiple connections are especially needed when the resistivity of the shell 24 or of the corresponding patterns is high. These connections prevent inefficient RF energy delivery due to RF voltage drops along parts of the shell 24 or the corresponding patterns.

In a preferred embodiment of the cap or bull's-eye pattern (see FIGS. 28A and 28B), multiple signal wires 26 are lead through the interior of the body 22 and out through a center aperture 74 in the distal fixture 66. Multiple signal wires 26 are preferred, as multiple electrical connections provide a more uniform current density distribution on the shell 24 than a single connection.

The signal wires 26 are enclosed within electrical insulation 160 (see FIG. 28B) except for their distal ends. There, the electrical insulation 160 is removed to expose the electrical conductor 162. The exposed electrical conductor 162 is also preferably flattened by mechanical means to provide an increased surface area. The flattened conductors 162 are affixed by an electrically conductive adhesive proximate to the geometric center and elsewhere at additional uniformly spaced intervals about it on the cap pattern, as well as along the geometric center of the concentric bands of the bull's-eye pattern, which the shell 24, when deposited, will create.

It is preferred that the adhesive connections of the conductors 162 to the body 22 be positioned, when possible, relatively close to an established support area on body 22, such as provided by the distal fixture 66. The support that the fixture 66 provides is a more secure attachment area for the electrical connections.

After the electrical connections are made, the shell 24 is deposited in the desired pattern on the body 22, over the adhesively attached conductors 162, in a manner previously described. The center aperture 74 in the distal fixture 66 is sealed closed by adhesive or equivalent material.

In an alternative embodiment (as FIGS. 29A/B show), the distal fixture 66 can also be used to create a mechanical connection to electrically couple a single signal wire 26 to the geometric center of the cap of the bull's-eye pattern. In the arrangement, the fixture 66 is made from an electrically conductive material. As FIGS. 29A/B show, the signal wire 26 is connected by spot welding, soldering, or electrically conductive adhesive to the fixture 66 within the expandable-collapsible body 22. A nut 74 engaging a threaded fixture end 164 sandwiches the distal tip of the body 22 between it and the collar 68 (see FIG. 29B). Epoxy, which could be electrically conductive, could be used to further strengthen the mechanical connection between the nut 74 and the body 22 sandwiched beneath it. The shell 24 is next deposited on the body 22 and nut 74 in a manner previously described.

Alternatively, the shell 24 can be deposited on the body 22 before attachment of the nut 74. In this arrangement, the nut 74 sandwiches the shell 24 between it and the collar 68, mechanically establishing the desired electrical connection between the signal wire 26 and the shell 24.

Alternatively, instead of a threaded nut connection, a heat shrunk slip ring of nickel titanium material can be used. Essentially, any riveting, swagging, electrically conductive plating, or bonding technique can be used to hold the shell 24 in contact against the collar 68.

It should be appreciated that additional solid fixtures 66 and associated electrical connection techniques can be used in other regions of the shell 22 distant from the distal tip of the body 22 to establish electrical contact in the circumferential bands of the bull's-eye pattern or proximate the geometric center and elsewhere on the circumferential segments. However, electrical connections can be made in these regions without using fixtures 66 or equivalent structural elements.

For example, as FIG. 30 shows, insulated signal wires 26 passed into the interior of the body can be snaked through the body 22 at the desired point of electrical connection. As before described, the electrical insulation 160 of the distal end of the snaked-through wire 26 is removed to the electrical conductor 162, which is also preferably flattened. As also before described, the flattened conductors 162 are affixed by an electrically conductive adhesive 172 to body 22, over which the shell 24 is deposited. Adhesive 172 is also preferably applied in the region of the body 22 where the wire 26 passes to seal it. As FIG. 31 shows, the same signal wire 26 can be snaked through the body 22 multiple times to establish multiple electrical connections within the same ablation zone.

In conjunction with any ablation zone pattern (see FIG. 32), the expandable-collapsible body 22 can be formed as a laminate structure 90. The laminate structure 90 comprises a base layer 92, formed from an electrically insulating material which peripherally surrounds the interior of the body 22. The laminate structure 90 further includes one or more intermediate layers 94 formed on the base layer 92. An ablation energy wire 26 passes through each intermediate layer 94. Each intermediate layer 94 is itself bounded by a layer 96 of electrically insulating material, so that the wires 26 are electrically insulated from each other. The laminate structure 90 also includes an outer layer 98 which is likewise formed from an electrically insulating material.

The laminate structure 90 can be formed by successively dipping a mold having the desired geometry in a substrate solution of electrically insulating material. The ablation energy wires 26 are placed on substrate layers between successive dippings, held in place by electrically conductive adhesive or the like.

After molding the laminated structure 90 into the desired geometry, one or more windows 100 are opened through the outer insulation layer 98 in the region which the electrically conductive shell 24 will occupy. Each window 100 exposes an ablation energy signal wire 26 in a chosen layer.

Various windowing techniques can be employed for this purpose. For example, $CO_2$ laser, Eximer laser, YAG laser, high power YAG laser, or other heating techniques can be used to remove insulation to the desired layer and thereby expose the desired signal wire 26.

After windowing, the formed expandable-collapsible body 22 is masked, as before described. The shell 24 of electrically conductive material is deposited over the unmasked area, including the windows 100, which have been previously opened.

As FIG. 32 shows, the deposited shell 24 enters the windows 100, making electrically conductive contact with the exposed wires 26. A plating or other deposition process may be used in the window 100, before depositing the electrically conductive shell 24. The plating fills in the window 100 to assure good electrical contact with the over-deposit of shell 24.

FIG. 3D shows an alternative equivalent laminated structure, in which the chamber 124 occupies the interior of the body 22. This creates a multiple layer structure equivalent to the laminated structure just described. An open intermediate layer 126 exists between the interior of the body 22 and the exterior of the chamber 124, through which signal wires 26 can be passed for electrical connection to the shell 24. The electrical connection can be made using either a distal fixture 66 or by snaking the wires through the exterior body 22 (as FIG. 3D shows), both of which have already been described.

V. Temperature Sensing

A. Connection of Temperature Sensors

As before described (see FIG. 1), a controller 32 preferably governs the conveyance of radio frequency ablation energy from the generator 30 to the shell 24. In the preferred embodiment, the collapsible electrode structure 20 carries one or more temperature sensing elements 104, which are coupled to the controller 32. Temperatures sensed by the temperature sensing elements 104 are processed by the controller 32. Based upon temperature input, the controller adjusts the time and power level of radio frequency energy transmissions by the shell 24, to achieve the desired lesion patterns and other ablation objectives.

The temperature sensing elements 104 can take the form of thermistors, thermocouples, or the equivalent. A temperature sensing element 104 may be located within the distal fixture 66 to sense temperature at the distal tip, as FIG. 33 shows. Alternatively, multiple temperature sensing elements may be scattered at spaced apart locations on the shell 24 or expandable-collapsible body 22, as FIG. 34 shows.

The connection of temperature sensing elements 104 to the shell 24 or expandable-collapsible body 22 can be achieved in various ways.

As shown in FIG. 34, when the expandable-collapsible body 22 comprises a thermally conductive material, the temperature sensing element (designated 104A in FIG. 34) can be attached to the interior surface of the body 22 in the region where measurement of exterior surface temperature is desired. A thermally conductive, but electrically insulating adhesive 106, can be used to secure the temperature sensing element 104A to the inside of the body 22. The temperature sensing element wires 110 extend through the catheter tube 12 for coupling (using a suitable connector 28, shown in FIG. 1) to the controller 32.

Alternatively, the temperature sensing element (designated 104B and 104C in FIG. 34) can be attached to the exterior surface of the body 22 in the region where measurement of temperatures is desired. As just described, a thermally conductive, but electrically insulating adhesive 106, can be used to secure the temperature sensing element to the outside of the body 22.

As shown with element 104B, the electrically conductive shell 24 can be deposited over the temperature sensing element 104B, in the manner previously described. In this way, the temperature sensing element 104B resides under the electrically conductive shell 24, and no discontinuities in the shell 24 are present.

Alternatively, as shown with element 104C, the element 104C can be masked at the time the electrically conductive shell 24 is deposited. In this arrangement, there is no electrically conductive material over the temperature sensing element 104C.

The signal wires 110 attached to the temperature sensing element 104C can be attached by electrically insulating adhesive to the outside of the expandable-collapsible body 22. Alternatively, as shown by element 104B, the signal wires 110 can be brought from the interior of the expandable-collapsible body 22 through the expandable-collapsible body 22 for attachment by a thermally conductive, but electrically insulating adhesive 106 to the outside of the body 22. The same type of adhesive 106 can also be used to anchor in signal wires 110 to the inside of the expandable-collapsible body 22.

As shown in FIG. 35, temperature sensing thermocouples 112 may also be integrally formed by deposition on the expandable-collapsible body. In this embodiment, the body 22 comprises a laminated structure 114, like that previously shown in FIG. 31, comprising a base layer 92, an outer layer 98, and one or more intermediate layers 94. In the laminate structure 114, the intermediate layers 94 formed in this structure comprise thermocouple wires 116 (t-type or other combinations). Before depositing the electrically conductive shell 24, windowing of the laminated expandable-collapsible body 116 in the manner previously described exposes the thermocouple wires. A conducting material 118, which, for a t-type thermocouple is copper or constantan, is deposited over the exposed thermocouple wires, forming the thermocouple 112. An electrically insulating material 120, like aluminum oxide or silicon dioxide, is then applied over the thermocouple 112.

The electrically conducting shell 24 can be deposited over the formed thermocouple 112. In this way, the thermocouples reside under the electrically conductive shell 24, and no discontinuities in the shell 24 are present. Alternatively, as thermocouple 112A shows in FIG. 35, the thermocouple 112A can be masked at the time the electrically conductive shell 24 is deposited. In this arrangement, there is no electrically conductive material over the thermocouple 112A.

B. Location of Temperature sensing Elements

Preferably, as FIGS. 20 and 21A/B show, multiple temperature sensing elements 104 are located on and about the shell 24 to ascertain temperature conditions during radio frequency energy ablation. The controller 32 uses temperature information from temperature sensing elements to control the transmission of ablation energy by the shell 24.

Generally speaking, at least one temperature sensing element 104 is preferably placed proximal to the geometric center of the energy transmitting shell 24. When the shell 24 is segmented (as FIGS. 20 and 21A/B show), at least one temperature sensing element 104 should be proximal to the geometric center of each energy transmitting segment 122.

Preferably, as FIGS. 20 and 21A/B further show, temperature sensing elements 104 are also placed along the edges of the shell 24, where it adjoins a masked, electrically non-conductive region of the body 22. When the shell 24 is segmented, temperature sensing elements 104 should be placed along the edge of each energy transmitting segment 122. High current densities occur along these regions where energy transmitting material adjoins non-energy transmitting material. These edge effects lead to higher temperatures at the edges than elsewhere on the shell 24. Placing temperature sensing elements 104 along the edges assures that the hottest temperature conditions are sensed.

In the case of a shell 24 segmented into adjacent energy transmitting zones 122, it is also desirable to place at least one temperature sensing element 104 between adjacent energy transmitting zones, as FIGS. 20 and 21A/B show. Placing multiple temperature sensing elements 104 in the segments 122, between the segments 122, and along the edges of the segments 122 allows the controller 32 to best govern power distribution to the multiple segments 122 based upon predictions of hottest temperature conditions. Further details of the use of multiple temperature sensing elements, including edge temperature sensing elements, and the use of temperature prediction methodologies, are found in copending U.S. patent application Ser. No. 08/439,824, filed May 12, 1995, and entitled "Systems and Methods for Controlling Tissue Ablation Using Multiple Temperature Sensing Elements."

The presence of segmented energy transmission zones 122, each with its own prescribed placement of temperature sensing elements 104, allows the controller 32 to govern the delivery of power to each zone 122 separately. The controller 32 is thereby able to take into account and react to differences in convective cooling effects in each zone 122 due to blood flow, differences in contact pressure and surface area between each zone 122 and the tissue that it contacts, and other nonlinear factors affecting the power required to heat tissue adjacent each zone 122 to a predetermined temperature to achieve the desired lesion geometry and pattern.

Thus, whereas for any given transmission zone (like the continuous, non-segmented shell 24 shown in FIG. 25 or each segmented zone 122 shown in FIGS. 26 and 27), it is desirable to allow some contact with the blood pool to allow beneficial convective cooling effects, it is not desirable that any given zone contact only or substantially only the blood pool. Loss of power into the blood pool with no tissue ablation effects occurs. With segmented zones 122, it is possible to sense, using the temperature sensing elements 104, where insubstantial tissue contact exists. It is thereby possible to sense and to channel available power only to those zones 122 where substantial tissue contact exists. Further details of tissue ablation using segmented electrode structures are disclosed in copending U.S. patent application Ser. No. 08/139,304, filed Oct. 19, 1993 and entitled "Systems and Methods for Creating Lesions in Body Tissue Using Segmented Electrode Assemblies."

Further details of the use of multiple ablation energy transmitters controlled using multiple temperature sensing elements are disclosed in copending U.S. patent No. application Ser. No. 08/286,930, filed Aug. 8, 1994, and entitled "Systems and Methods for Controlling Tissue Ablation Using Multiple Temperature Sensing Elements".

FIG. 36 shows a preferred representative embodiment when the shell 24 comprises a continuous cap pattern. In this arrangement, the structure 20 carries five temperature sensing elements 104 spaced apart on the shell 24. The temperature sensing elements 104 are connected in a selected one or more of the manners previously described.

Preferably, sensing elements $Tn_1$ and $Tn_2$ are placed at diametrically opposite regions at the most proximal edge of the shell 24. Sensing elements $Tm_1$ and $Tm_2$ are placed at diametrical sides of the middle region of the shell 24, for example, at about 50% of the radius of the structure. The sensor Tc is placed proximal the geometric center of the shell 24. All temperature sensors are coupled to a temperature controller, which processes information from the sensors.

In this arrangement, the temperature controller 32 infers the percentage of tissue contact with the shell 24 contact based upon where significant increases in temperature conditions from an established baseline level (for example, 37° C.) are sensed on the shell 24. These increased temperature conditions indicate the absence of convective cooling effects, as would occur with contact with the blood pool, thereby suggesting tissue contact. As the preceding Tables 1 and 2 show, percentage of contact between the shell 24 and tissue dictate effective power levels to achieve the type of lesion desired.

The relationship between percentage shell-tissue contact and power desired for a given lesion characteristic can be based upon empirical or theoretical data in the manner set forth in the preceding Example. These relationships can be set forth in look up table format or incorporated in equivalent decision matrices, which the controller 32 retains in memory.

For example, if large deep lesions are desired, significant increase in temperature above the baseline at Tc, but not elsewhere, indicates a 20% tissue contact condition, and a first power level is commanded for the generator 30 based upon the selected power criteria. Significant increase in temperature above the baseline also at $Tm_1$ and $Tm_2$ indicates a 50% tissue contact condition, and second power level less than the first is commanded for the generator 30 based upon the selected power criteria. Significant increase in temperature above the baseline also at $Tn_1$ and $Tn_2$ indicates a 100% tissue contact condition, and third power level less than the second is commanded based upon the selected power criteria.

FIG. 37 shows a preferred representative embodiment when the shell 24 comprises a circumferentially spaced, segmented pattern. In this arrangement, the structure 20 carries at least four temperature sensing elements on each shell segment.

The sensor Tc is common to all segments and is located at the distal end of the pattern. The sensor $T_{GC}$ is located at the geometric center of each segment, while the sensors $T_{E1}$ and $T_{E2}$ are located along opposite edges of each segment, where the shell 24 adjoins the non-electrically conductive regions separating the segments. An additional sensor $T_M$ is preferably also located generally between the segments for the reasons discussed before.

FIG. 38 shows a preferred representative embodiment when the shell 24 comprises a bull's-eye pattern. Sensors $T_{GC}$ are located at the geometric center of each segment of the pattern, while the sensors $T_{E1}$ and $T_{E2}$ are located along opposite edges of each segment, where the shell 24 adjoins the non-electrically conductive regions separating the segments. An additional sensor $T_M$ is preferably also located generally between the segments for the reasons discussed before.

VI. Active Cooling

The capability of the shell 24 to form large lesions can be enhanced by actively cooling the shell 24 while transmitting ablation energy.

Active cooling can be accomplished by the use of multiple lumens to cycle a cooled fluid through the expandable-collapsible body 22 while transmitting ablation energy. Alternatively, a high pressure gas can be transported by the lumens for expansion within the expandable-collapsible body to achieve a comparable active cooling effect. In yet another alternative arrangement, the cooled medium can be conveyed outside the expandable-collapsible body 22 to achieve an active cooling effect.

With active cooling, more power can be applied, while maintaining the same maximum tissue temperature conditions, thereby creating larger and deeper lesions. With active cooling, the percentage contact of the shell 24 with tissue relative to blood can be increased above 50%, and may be as much as 100%.

Further details concerning the use of active cooling to enhance lesion formation are found in copending U.S. patent No. application Ser. No. 08/431,790, filed May 1, 1995, and entitled "Systems and Methods for Obtaining Desired Lesion Characteristics While Ablating Body Tissue".

It should be appreciated that the entire surface of the shell 24 need not be cooled to achieve at least some of the benefits of active cooling. For example, only selected regions of the shell 24 which are prone to localized edge heating effects, as previously described, can be subjected to active cooling. The edge effects on current densities occur at the boundary between the shell 24 and expandable-collapsible body 22 that is free of the shell 24 create higher temperatures. Localized cooling of these edge regions can help minimize the effects of hot spots on lesion formation.

In this arrangement, as FIG. 39 shows, a pattern of small holes 174 is created in the region between segmented shell patterns 122. Liquid cooling medium is perfused from inside the body 22 through the holes 174 to provide localized cooling adjacent the edges of the shell segments 122. It should be appreciated that hole patterns 174 could be used elsewhere on the body 22 to provide active cooling effects.

As FIGS. 39, 40A and 40B show, the selective establishment of hole patterns 174 on the body 22 can also itself establish predefined fold lines 52, eliminating the need to specially mold preformed folding regions the body 22. The pattern of small holes 174 create fold lines 52 by the removal of material, thereby increasing the flexibility of the body 22 along the holes 174 between adjacent regions 122. In this arrangement (see FIG. 39), the fold lines 52 created by hole patterns 174 lie uniformly along (i.e., parallel to) the long axis of the body 22.

VII. Obtaining Desired Lesion Characteristics

As Tables 1 and 2 in the foregoing Example demonstrate, the same expandable-collapsible electrode structure 20 is able to selectively form lesions that are either wide and shallow or large and deep. Various methodologies can be used to control the application of radio frequency energy to the shell 24 of the body 20 to achieve this result.

A. $D_{50C}$ Function

In one representative embodiment, the controller 32 includes an input 300 for receiving from the physician a desired therapeutic result in terms of (i) the extent to which the desired lesion should extend beneath the tissue-electrode interface to a boundary depth between viable and nonviable tissue and/or (ii) a maximum tissue temperature developed within the lesion between the tissue-electrode interface and the boundary depth.

The controller 32 also includes a processing element 302, which retains a function that correlates an observed relationship among lesion boundary depth, ablation power level, ablation time, actual or predicted sub-surface tissue temperature, and electrode temperature. The processing element 302 compares the desired therapeutic result to the function and selects an operating condition based upon the comparison to achieve the desired therapeutic result without exceeding a prescribed actual or predicted sub-surface tissue temperature.

The operating condition selected by the processing element 302 can control various aspects of the ablation procedure, such as controlling the ablation power level, the rate at which the structure 20 is actively cooled, limiting the ablation time to a selected targeted ablation time, limiting the ablation power level subject to a prescribed maximum ablation power level, and/or the orientation of the shell 24, including prescribing a desired percentage contact between the shell 24 and tissue. The processing element 302 can rely upon temperature sensors carried by or otherwise associated with the expandable-collapsible structure 20 that penetrate the tissue to sense actual maximum tissue temperature. Alternatively, the processing element 302 can predict maximum tissue temperature based upon operating conditions.

In the preferred embodiment, the electrode structure 20 carries at least one temperature sensing element 104 to sense instantaneous localized temperatures (T1) of the thermal mass of the shell 24. The temperature T1 at any given time is a function of the power supplied to the shell 24 by the generator 30 and the rate at which the shell 24 is cooled, either by convective cooling by the blood pool, or active cooling by another cooling medium brought into contact with the shell 24, or both.

The characteristic of a lesion can be expressed in terms of the depth below the tissue surface of the 50° C. isothermal region, which will be called $D_{50C}$. The depth $D_{50C}$ is a function of the physical characteristics of the shell 24 (that is, its electrical and thermal conductivities and size); the percentage of contact between the tissue and the shell 24; the localized temperature T1 of the thermal mass of the shell 24; the magnitude of RF power (P) transmitted by the shell 24 into the tissue, and the time (t) the tissue is exposed to the RF power.

For a desired lesion depth D50C, additional considerations of safety constrain the selection of an optimal operating condition among the operating conditions listed in the matrix. The principal safety constraints are the maximum tissue temperature TMAX and maximum power level PMAX.

The maximum temperature condition TMAX lies within a range of temperatures which are high enough to provide deep and wide lesions (typically between about 85° C. and 95° C.), but which are safely below about 100°0 C., at which tissue desiccation or tissue micro-explosions are known to occur. It is recognized that TMAX will occur a distance below the electrode-tissue interface between the interface and $D_{50C}$.

The maximum power level PMAX takes into account the physical characteristics of the electrode and the power generation capacity of the RF generator 30.

These relationships can be observed empirically and/or by computer modeling under controlled real and simulated conditions, as the foregoing examples illustrate. The D50C function for a given shell 24 can be expressed in terms of a matrix listing all or some of the foregoing values and their relationship derived from empirical data and/or computer modeling.

The processing element 302 includes in memory this matrix of operating conditions defining the D50C temperature boundary function, as described above for t=120 seconds and TMAX=95° C. and for an array of other operating conditions.

The physician also uses the input 300 to identify the characteristics of the structure 20, using a prescribed identification code; set a desired maximum RF power level PMAX; a desired time t; and a desired maximum tissue temperature TMAX.

Based upon these inputs, the processing element 302 compares the desired therapeutic result to the function defined in the matrix (as exemplified by the above Tables 1 and 2). The master controller 58 selects an operating condition to achieve the desired therapeutic result without exceeding the prescribed TMAX by controlling the function variables.

This arrangement thereby permits the physician, in effect, to "dial-a-lesion" by specifying a desired $D_{50C}$. By taking into account the effects of convective cooling based upon percentage of shell contact with tissue and by using active cooling in association with time and power control, the processing element can achieve the desired $D_{50C}$ without the need to sense actual tissue temperature conditions.

Further details of deriving the $D_{50C}$ function and its use in obtaining a desired lesion pattern are found in copending U.S. application Ser. No. 08/431,790, filed May 1, 1995, entitled "Systems and Methods for Obtaining Desired Lesion Characteristics While Ablating Body Tissue," which is incorporated herein by reference.

B. Predicting Maximum Tissue Temperature

The structure 20 is cooled either by convective blood flow (depending upon percentage contact between the shell 24 and tissue), or by actively using another cooling medium, or both. The level of RF power delivered to the cooled structure 20 and/or the cooling rate can be adjusted based upon a prediction of instantaneous maximum tissue temperature, which is designated $\Psi_{MAX}(t)$.

In a preferred implementation, the prediction of $\Psi_{MAX}$ is derived by a neural network, which has as inputs a prescribed number of previous power levels, previous rates at which heat has been removed to cool the structure 20, and previous shell temperature.

The heat removal rate is identified by the expression Å, where $$Å = c \times \Delta T \times \text{RATE}$$

where:

c is the heat capacity of the cooling medium used (in Joules (J) per kilogram (kg) Kelvin (K), or J/kg K)

$\Delta T$ is the temperature drop in the cooling medium during passing through the structure 20 (K), and RATE is the mass flow rate of the cooling medium through the structure (kg/sec).

The heat generated by the structure 20 into the tissue is the difference between the heat generated by Joule effect and the heat removed by cooling. At a given localized shell temperature T1 and flow rate of cooling medium, the magnitude of Å increases as RF power delivered to the shell 24 increases. Together, T1 and Å represent an indirect measurement of how rapidly the sub-surface tissue temperature is changing. Together, T1 and Å are therefore predictive of the depth and magnitude of the hottest sub-surface tissue temperature $\Psi_{MAX}$, and thus indirectly predictive of the lesion boundary depth $D_{50C}$. Large deep lesions are predicted when T1 is maintained at a low relative temperature (by controlling cooling rate) and the maximal predicted tissue temperature, TMAX, is maintained at approximately 85° C. to 95° C. by controlling RF power. Likewise, more shallow lesions are predicted when T1 is maintained at a high relative temperature and TMAX is maintained at lower values.

Further details of deriving the this prediction function and its use in obtaining a desired lesion pattern are found in copending U.S. application Ser. No. 08/431,790, filed May 1, 1995, entitled "Systems and Methods for Obtaining Desired Lesion Characteristics While Ablating Body Tissue," which is incorporated herein by reference.

C. Segmented Shells: Duty Cycle Control

Various RF energy control schemes can also be used in conjunction with segmented shell patterns shown in FIG. 20 (the axially spaced, bull's-eye pattern of zones) and FIGS. 21 and 22 (the circumferentially spaced zones) For the purpose of discussion, the zones (which will also be called electrode regions) 122 will be symbolically designated E(J), where J represents a given zone 122 (J=1 to N).

As before described, each electrode region E(J) has at least one temperature sensing element 104, which will be designated S(J,K), where J represents the zone and K represents the number of temperature sensing elements on each zone (K=1 to M).

In this mode, the generator 30 is conditioned through an appropriated power switch interface to deliver RF power in multiple pulses of duty cycle 1/N.

With pulsed power delivery, the amount of power ($P_{E(J)}$) conveyed to each individual electrode region E(J) is expressed as follows:

$$P_{E(J)} \alpha AMP_{E(J)}^2 \times DUTYCYCLE_{E(J)}$$

where:

$AMP_{E(J)}$ is the amplitude of the RF voltage conveyed to the electrode region E(J), and $DUTYCYCLE_{E(J)}$ is the duty cycle of the pulse, expressed as follows:

$$DUTYCYCLE_{E(J)} = \frac{TON_{E(J)}}{TON_{E(J)} + TOFF_{E(J)}}$$

where:

$TON_{E(J)}$ is the time that the electrode region E(J) emits energy during each pulse period, $TOFF_{E(J)}$ is the time that the electrode region E(J) does not emit energy during each pulse period.

The expression $TON_{E(J)} + TOFF_{E(J)}$ represents the period of the pulse for each electrode region E(J).

In this mode, the generator 30 can collectively establish duty cycle ($DUTYCYCLE_{E(J)}$) of 1/N for each electrode region (N being equal to the number of electrode regions).

The generator 30 may sequence successive power pulses to adjacent electrode regions so that the end of the duty cycle for the preceding pulse overlaps slightly with the beginning of the duty cycle for the next pulse. This overlap in pulse duty cycles assures that the generator 30 applies power continuously, with no periods of interruption caused by open circuits during pulse switching between successive electrode regions.

In this mode, the temperature controller 32 makes individual adjustments to the amplitude of the RF voltage for each electrode region ($AMP_{E(J)}$), thereby individually changing the power $P_{E(J)}$ of ablating energy conveyed during the duty cycle to each electrode region, as controlled by the generator 30.

In this mode, the generator 30 cycles in successive data acquisition sample periods. During each sample period, the generator 30 selects individual sensors S(J,K), and temperature codes TEMP(J) (highest of S(J,K)) sensed by the sensing elements 104, as outputted by the controller 32.

When there is more than one sensing element associated with a given electrode region (for example, when edge-located sensing elements are used), the controller 32 registers all sensed temperatures for the given electrode region and selects among these the highest sensed temperature, which constitutes TEMP(J).

In this mode, the generator 30 compares the temperature TEMP(J) locally sensed at each electrode E(J) during each data acquisition period to a set point temperature $TEMP_{SET}$ established by the physician. Based upon this comparison, the generator 30 varies the amplitude $AMP_{E(J)}$ of the RF voltage delivered to the electrode region E(J), while maintaining the $DUTYCYCLE_{E(J)}$ for that electrode region and all other electrode regions, to establish and maintain TEMP(J) at the set point temperature $TEMP_{SET}$.

The set point temperature $TEMP_{SET}$ can vary according to the judgment of the physician and empirical data. A representative set point temperature for cardiac ablation is believed to lie in the range of 40° C. to 95° C., with 70° C. being a representative preferred value.

The manner in which the generator 30 governs $AMP_{E(J)}$ can incorporate proportional control methods, proportional integral derivative (PID) control methods, or fuzzy logic control methods.

For example, using proportional control methods, if the temperature sensed by the first sensing element TEMP(1) > $TEMP_{SET}$, the control signal generated by the generator 30 individually reduces the amplitude $AMP_{E(1)}$ of the RF voltage applied to the first electrode region E(1), while keeping the duty cycle $DUTYCYCLE_{E(1)}$ for the first electrode region E(1) the same. If the temperature sensed by the second sensing element TEMP(2) < $TEMP_{SET}$, the control signal of the generator 30 increases the amplitude $AMP_{E(2)}$ of the pulse applied to the second electrode region E(2), while keeping the duty cycle $DUTYCYCLE_{E(2)}$ for the second electrode region E(2) the same as $DUTYCYCLE_{E(1)}$, and so on. If the temperature sensed by a given sensing element is at the set point temperature $TEMP_{SET}$, no change in RF voltage amplitude is made for the associated electrode region.

The generator continuously processes voltage difference inputs during successive data acquisition periods to individually adjust $AMP_{E(J)}$ at each electrode region E(J), while keeping the collective duty cycle the same for all electrode regions E(J). In this way, the mode maintains a desired uniformity of temperature along the length of the ablating element.

Using a proportional integral differential (PID) control technique, the generator takes into account not only instantaneous changes that occur in a given sample period, but also changes that have occurred in previous sample periods and the rate at which these changes are varying over time. Thus, using a PID control technique, the generator will respond differently to a given proportionally large instantaneous difference between TEMP (J) and $TEMP_{SET}$, depending upon whether the difference is getting larger or smaller, compared to previous instantaneous differences, and whether the rate at which the difference is changing since previous sample periods is increasing or decreasing.

Further details of individual amplitude/collective duty cycle control for segmented electrode regions based upon temperature sensing are found in copending U.S. application Ser. No. 08/439,824, filed May 12, 1995 and entitled "Systems and Methods for Controlling Tissue Ablation Using Multiple Temperature Sensing Elements," which is incorporated herein by reference.

D. Segmented Shells: Differential Temperature Disabling

In this control mode, the controller 32 selects at the end of each data acquisition phase the sensed temperature that is the greatest for that phase ($TEMP_{SMAX}$). The controller 32 also selects for that phase the sensed temperature that is the lowest ($TEMP_{SMIN}$).

The generator compares the selected hottest sensed temperature $TEMP_{SMAX}$ to a selected high set point temperature $TEMP_{HISET}$. The comparison generates a control signal that collectively adjusts the amplitude of the RF voltage for all electrodes using proportional, PID, or fuzzy logic control techniques.

In a proportion control implementation scheme:

(i) If $TEMP_{SMAX} > TEMP_{HISET}$, the control signal collectively decreases the amplitude of the RF voltage delivered to all segments;

(ii) If $TEMP_{SMAX}<TEMP_{HISET}$, the control signal collectively increases the amplitude of the RF voltage delivered to all segments;

(iii) If $TEMP_{SMAX}=TEMP_{HISET}$, no change in the amplitude of the RF voltage delivered to all segments.

It should be appreciated that the generator can select for amplitude control purposes any one of the sensed temperatures $TEMP_{SMAX}$, $TEMP_{SMIN}$, or temperatures in between, and compare this temperature condition to a preselected temperature condition.

The generator governs the delivery of power to the segments based upon difference between a given local temperature TEMP (J) and $TEMP_{SMIN}$. This implementation computes the difference between local sensed temperature TEMP(J) and $TEMP_{SMIN}$ and compares this difference to a selected set point temperature difference $\Delta TEMP_{SET}$. The comparison generates a control signal that governs the delivery of power to the electrode regions.

If the local sensed temperature TEMP(J) for a given electrode region E(J) exceeds the lowest sensed temperature $TEMP_{SMIN}$ by as much as or more than $\Delta TEMP_{SET}$ (that is, if $TEMP(J)-TEMP_{SMIN} \geq \Delta TEMPSET$), the generator turns the given segment E(J) off. The generator turns the given segment E(J) back on when $TEMP(J)-TEMP_{SMIN}<\Delta TEMP_{SET}$.

Alternatively, instead of comparing TEMP(J) and $TEMP_{SMIN}$, the generator can compare $TEMP_{SMAX}$ and $TEMP_{SMIN}$. When the difference between $TEMP_{SMAX}$ and $TEMP_{SMIN}$ equals or exceeds a predetermined amount $\Delta TEMP_{SET}$, the generator turns all segments off, except the segment where $TEMP_{SMIN}$ exists. The controller 231 turns these segments back on when the temperature difference between $TEMP_{SMAX}$ and $TEMP_{SMIN}$ is less than $\Delta TEMP_{SET}$.

Further details of the use of differential temperature disabling are found in copending U.S. patent application Ser. No. 08/286,930, filed Aug. 8, 1994, and entitled "Systems and Methods for Controlling Tissue Ablation Using Multiple Temperature Sensing Elements," which is incorporated herein by reference.

E. Segmented Shells (Predicted Hottest Temperature)

Because of the heat exchange between the tissue and the electrode region 122, the temperature sensing elements 104 may not measure exactly the maximum temperature at the region 122. This is because the region of hottest temperature occurs beneath the surface of the tissue at a depth of about 0.5 to 2.0 mm from where the energy emitting electrode region 122 (and the associated sensing element 104) contacts the tissue. If the power is applied to heat the tissue too quickly, the actual maximum tissue temperature in this subsurface region may exceed 100° C. and lead to tissue desiccation and/or micro-explosions.

Figure 43:
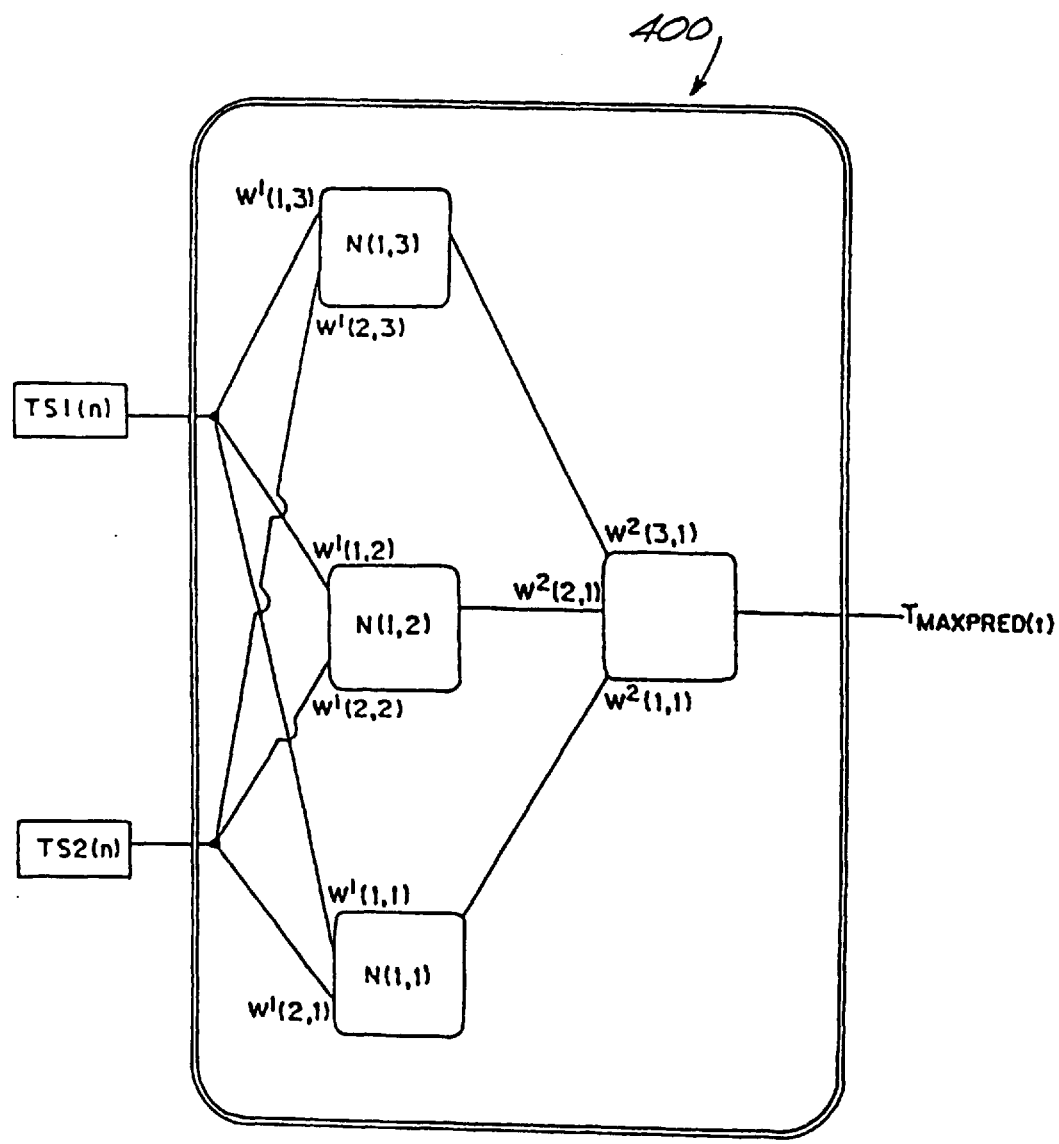
FIG. 43 is a diagrammatic view of neural network usable for predicting maximum temperature conditions when the expandable-collapsible electrode structure carries multiple ablation energy transmitting segments.

FIG. 43 shows an implementation of a neural network predictor 400, which receives as input the temperatures sensed by multiple sensing elements S(J,K) at each electrode region, where J represents a given electrode region (J=1 to N) and K represents the number of temperature sensing elements on each electrode region (K=1 to M). The predictor 400 outputs a predicted temperature of the hottest tissue region $T_{MAXPRED}$ (t). The generator 30 derives the amplitude and duty cycle control signals based upon $T_{MAXPRED}$ (t), in the same manner already described using TEMP(J).

The predictor 400 uses a two-layer neural network, although more hidden layers could be used. As shown in FIG. 43, the predictor 300 includes a first and second hidden layers and four neurons, designated $N_{(L,X)}$, where L identifies the layer 1 or 2 and X identifies a neuron on that layer. The first layer (L=1) has three neurons (X=1 to 3), as follows $N_{(1,1)}$; $N_{(1,2)}$; and $N_{(1,3)}$. The second layer (L=2) comprises one output neuron (X=1), designated $N_{(2,1)}$.

Temperature readings from the multiple sensing elements, only two of which—TS1(n) and TS2(n)—are shown for purposes of illustration, are weighed and inputted to each neuron $N_{(1,1)}$; $N_{(1,2)}$; and $N_{(1,3)}$ of the first layer. FIG. 43 represents the weights as $W^L_{(k,N)}$, where L=1; k is the input sensor order; and N is the input neuron number 1, 2, or 3 of the first layer.

The output neuron $N_{(2,1)}$ of the second layer receives as inputs the weighted outputs of the neurons $N_{(1,1)}$; $N_{(1,2)}$; and $N_{(1,3)}$. FIG. 43 represents the output weights as $W^L_{(O,X)}$, where L=2; O is the output neuron 1, 2, or 3 of the first layer; and X is the input neuron number of the second layer. Based upon these weighted inputs, the output neuron $N_{(2,1)}$ predicts $T_{MAXPRED}$ (t).

Alternatively, a sequence of past reading samples from each sensor could be used as input. By doing this, a history term would contribute to the prediction of the hottest tissue temperature.

The predictor 400 must be trained on a known set of data containing the temperature of the sensing elements TS1 and TS2 and the temperature of the hottest region, which have been previously acquired experimentally. For example, using a back-propagation model, the predictor 400 can be trained to predict the known hottest temperature of the data set with the least mean square error. Once the training phase is completed, the predictor 300 can be used to predict $T_{MAXPRED}$ (t).

Other types of data processing techniques can be used to derive $T_{MAXPRED}$ (t) See, e.g., copending patent application Ser. No. 08/266,934, filed Jun. 27, 1994, and entitled "Tissue Heating and Ablation Systems and Methods Using Predicted Temperature for Monitoring and Control."

The illustrated and preferred embodiments use digital processing controlled by a computer to analyze information and generate feedback signals. It should be appreciated that other logic control circuits using micro-switches, AND/OR gates, invertors, analog circuits, and the like are equivalent to the micro-processor controlled techniques shown in the preferred embodiments.

VIII. Capacitive Coupling

In the preceding embodiments, the electrode structure 20 transmits ablation energy to tissue by exposing tissue to an electrically conductive surface 24 carried about the exterior of the expandable-collapsible body 22. The alternative embodiments shown in FIGS. 41A and 42A include an electrode structure 176 comprising an expandable-collapsible body 178 having an exterior free of an electrically conductive surface. In these embodiments, the body 178 is capacitively coupled to tissue for the purpose of transmitting ablation energy.

In the embodiment shown in FIG. 41A, the expandable-collapsible body 178 is molded in the same fashion as the body 22 previously described. The body 178 includes an electrically conductive structure 180 in contact with at least a portion of the interior surface 182 of the body 178.

The interior conductive structure 180 can be assembled in various ways. In the embodiment shown in FIG. 41A, the structure 180 comprises an interior shell 184 of electrically conductive material deposited on at least a portion of the interior surface 182 of the body 178. Like the exterior shell 24 previously described, the interior shell 184 comprises a material having a relatively high electrical conductivity, as well as a relative high thermal conductivity, such as gold, platinum, platinum/iridium, among others. The shell 184 is preferably deposited upon the exterior of the body 178 after molding using deposition process like sputtering, vapor deposition, ion beam deposition, electroplating over a deposited seed layer, or a combination of these processes. The body 178 is then everted in the manner previously described (as FIG. 16B shows) to place the deposited shell 184 inside the everted body 178. One or more signal wires 186 are coupled to the interior shell 184 using electrically conductive adhesive, soldering, or equivalent connection techniques.

The body 178 can be caused to assume expanded and collapsed geometries by the introduction of an air or liquid inflation medium, as previously described. Alternatively, the body 178 can employ any previously described interior support structure 44 to affect expansion and collapse. The support structures 44 could also be electrically conductive to affect capacitive coupling, with or without the presence of the deposited shell 184. For example, an electrically conductive interior resilient mesh structure (like that shown in FIG. 6), or a skeleton of flexible, electrically conductive spline elements (like that shown in FIG. 4), or an open cell foam structure coated with an electrically conductive material (like that shown in FIG. 9), can be used both to provide interior support and to provide capacitive coupling between signal wires 186 and tissue, with or without the presence of the deposited interior shell 184. In these alternative arrangements, one or more signal wires 184 are coupled to the electrically conductive support structures.

FIG. 41B shows the electrical equivalent circuit 188 of the capacitive coupling effect that the structure 176 in FIG. 41A provides. In the electrical path 190 that the ablation energy 192 follows, the interface 194 formed among the expandable-collapsible body 178, the conductive structure 180 contacting the inside the body 178, and the tissue 196 contacting the outside of the body 178 functions as a capacitor (designated C), whose impedance $X_c$ is expressed as:

$$X_C = \frac{1}{2\pi f C}$$

where:

f is the frequency of the radio frequency ablation energy 192, and $$C = \epsilon \frac{s}{t}$$

where $\epsilon$ is the dielectric constant of the material of the expandable-collapsible body 178, which ranges from about 1.2 to about 10.0 (multiplied by $8.85 \times 10^{-12}$ Farads per meter) for most plastic materials, s is the surface area of the electrically conductive structure 184, and t is the thickness of the body 178 located between the electrically conductive structure 180 and the contacted tissue 196.

In the electrical path 190 that the ablation energy 192 follows, the tissue 196 functions as a resistor (designated $R_{TISSUE}$) series coupled to C. Typically, $R_{TISSUE}$ is about 100 ohms.

To have efficient capacitive coupling to the tissue, $X_c$ of the structure 180 must be less than $R_{TISSUE}$. This relationship assures that the desired ohmic heating effect is concentrated in tissue.

To maximize the capacitive coupling effect, it is thereby important to use ablation energy at higher frequencies (for example, between 10 and 20 Mhz). It is also important to aim to maximize C as much as possible, by controlling thickness of the body 178 as well as by maximizing as much as possible the surface area of contact with the electrically conductive structure 180 inside the body 178. For this reason, a continuous electrically conductive shell 182 or equivalent mesh structure are preferred, compared to a more open spline element structure. However, a more dense, conductive spline element structure having many spline elements and/or large surface area splines could be used to maximize C, if desired.

FIG. 42A shows an alternative embodiment of an expandable-collapsible electrode structure 198 that provides capacitive coupling to tissue. The structure 198 comprises an interior electrode 200 of electrically conductive material located within the interior of the body 178. The interior electrode 200 comprises a material having a relatively high electrical conductivity, as well as a relatively high thermal conductivity, such as gold, platinum, platinum/iridium, among others. A signal wire 202 is coupled to the electrode to conduct ablation energy to it.

In this embodiment, a hypertonic (i.e., 9%) saline solution 204 fills the interior of the body 178. The saline solution 204 serves as an electrically conductive path to convey radio frequency energy from the electrode 200 to the body 178. The saline solution 204 also serves as the inflation medium, to cause the body 178 to assume the expanded geometry. Removal of the saline solution 204 causes the body 178 to assume the collapsed geometry.

FIG. 42B shows the electrically equivalent circuit 206 of the capacitive coupling effect that the structure 198 shown in FIG. 42A provides. In the electrical path 208 that the ablation energy 210 follows, the interface 212 formed among the expandable-collapsible body 178, the hypertonic saline solution 204 contacting the inside the body 178, and the tissue 196 contacting the outside of the body 178 functions as a capacitor (designated C), whose impedance $X_c$ is expressed as:

$$X_C = \frac{1}{2\pi f C}$$

where:

f is the frequency of the radio frequency ablation energy 210, and $$C = \epsilon \frac{s_B}{t}$$

where $\epsilon$ is the dielectric constant of the material of the body 178, $S_B$ is the area of the body 178 contacting the hypertonic saline solution 204, and t is the thickness of the body 178 located between the electrically conductive saline solution 204 and the tissue 196.

In the electrical path that the ablation energy follows, the tissue 196 functions as a resistor (designated $R_{Tissue}$) series coupled to C, which value is about 100 ohms. The path 216 through the hypertonic saline 204 between the interior electrode 200 and the interior surface 214 of the body 178 also functions as a resistor (designated $R_{PATH}$) series coupled to C. The value of $R_{PATH}$ is expressed:

$$R_{PATH} = \frac{K}{S_E} \rho$$

where:

K is a constant that depends upon the geometry of the structure 198, $S_E$ is the surface area of the interior electrode 200, and $\rho$ is the resistivity of the hypertonic saline 204.

The following relationship establishes efficient capacitive coupling between the structure 198 and tissue 196 to achieve the desired ohmic tissue heating effect:

$$\sqrt{R_{PATH}^2 + X_C^2} < R_{TISSUE}$$

The use of capacitive coupling provides structural benefits. It isolates possible shell adherence problems to inside the body 178 of the structure 176, where flaking and chipping of the shell 184 can be retained out of the blood pool. Capacitive coupling also avoids potential problems that tissue sticking to exterior conductive materials could create.

In addition to these structural benefits, the temperature control of the ablation process (as described above in conjunction with the structure 20) is improved using capacitive coupling. When using a metal surface to ablate tissue, the tissue-electrode interface is convectively cooled by surrounding blood flow. Due to these convective cooling effects, the region of maximum tissue temperature is located deeper in the tissue. As a result, the temperature conditions sensed by sensing elements associated with metal electrode elements do not directly reflect actual maximum tissue temperature. In this situation, maximum tissue temperature conditions must be inferred or predicted from actual sensed temperatures, as set forth above. Using capacitive coupling in structures 176 or 198, convective cooling of the tissue-electrode interface by the surrounding blood flow is minimized. As a result, the region of maximum temperature is located at the interface between tissue and the porous electrode. As a result, the temperature conditions sensed by sensing elements associated with the capacitively coupled structures 176 or 198 will more closely reflect actual maximum tissue.

IX. Conductive Polymer Surfaces

As previously mentioned in conjunction with FIG. 19, all or a portion of the body 22 can comprise an electrically conductive polymer. The conductivity of the polymer used preferably has a resistivity close to the resistivity of tissue (i.e., about 500 ohm·cm). In use, the electrically conductive body 22 can be used in association with an interior electrode 200, like that shown in FIG. 42A. In such an arrangement, a hypertonic saline solution 204 also fills the interior of the electrically conductive body 22 (as also shown in FIG. 42A), to serve as an electrically conductive path to convey radio frequency energy from the electrode 200 to the body 22. In effect, in this arrangement, the electrically conductive body 22 functions as a "leaky" capacitor in transmitting radio frequency energy from the interior electrode 200 to tissue.

Various methodologies can be used to control the application of radio frequency energy to capacitively coupled electrode structures and to electrode structures having electrically conductive bodies. The previously described $D_{50C}$ Function can be used, as can the previously described Duty Cycle and Temperature Disabling techniques. With capacitively coupled electrode structures and electrode structures having electrically conductive bodies, the minimal effects of convective cooling by the blood pool enables the use of actual sensed temperature conditions as maximum tissue temperature TMAX, instead of predicted temperatures. Because of this, such structures also lend themselves to the use of a proportional integral differential (PID) control technique. Illustrative PID control techniques usable in association with these electrode structures are disclosed in copending U.S. patent application Ser. No. 08/266,023, filed Jun. 27, 1994, entitled "Tissue Heating and Ablation Systems and Methods Using Time-Variable Set Point Temperature Curves for Monitoring and Control."

Various features of the invention are set forth in the following claims.

We claim:

1. A folding electrode assembly comprising a structure comprising a wall peripherally enclosing an interior, the structure adapted to selectively assume a geometry that changes between an expanded geometry having a first maximum diameter and a collapsed geometry having a second maximum diameter less than the first maximum diameter, an electrically conductive material having resistivity carried by the wall adapted for transmitting ablation energy, the electrically conductive material conforming to both the expanded geometry and the collapsed geometry, and at least one folding region in the wall adapted to fold upon itself along a predefined fold line as the structure geometry changes, the at least one folding region having resistivity that is greater than about ten times the resistivity of the electrically conductive material.

2. An assembly according to claim 1 wherein the folding region is essentially free of electrically conductive material.

3. An assembly according to claim 1 wherein the folding region includes an electrical insulating material.

4. An assembly according to claim 1 and further including at least one temperature sensing element on the structure located proximal to where electrically conductive material adjoins the folding region.

5. An assembly according to claim 1 and further including at least one temperature sensing element on the structure located in the folding region.

6. An assembly according to claim 1 and further including at least one temperature sensing element on the structure located in the electrically conductive material.

7. An assembly according to claim 1 and further including at least one temperature sensing element on the structure located where the electrically conductive material adjoins the folding region.

8. An assembly according to claim 1 wherein the electrically conductive material comprises a coating deposited on the wall.

9. An assembly according to claim 1 wherein the electrically conductive material comprises foil affixed to the wall.

10. An assembly according to claim 1 wherein the electrically conductive material comprises material located within the wall.

11. An assembly according to claim 10 wherein the electrically conductive material comprises an electrically conductive shell on the wall.

12. An assembly according to claim 1 and further including a radiopaque material carried by the structure.

13. A folding electrode assembly comprising
a structure comprising a wall peripherally enclosing an interior, the structure adapted to selectively assume a geometry that changes between an expanded geometry having a first maximum diameter and a collapsed geometry having a second maximum diameter less than the first maximum diameter,
at least two spaced apart zones of electrically conductive material having resistivity carried by the wall adapted for transmitting ablation energy, the electrically conductive material in the at least two zones conforming to both the expanded geometry and the collapsed geometry, and
a folding region in the wall between the spaced apart zones adapted to fold upon itself along a predefined fold line as the structure geometry changes, the folding region having resistivity that is greater than about ten times the resistivity of the electrically conductive material.

14. An assembly according to claim 13 wherein the folding region is essentially free of electrically conductive material.

15. An assembly according to claim 13 wherein the folding region includes an electrical insulating material.

16. An assembly according to claim 13 wherein the electrically conductive material comprises a coating deposited on the wall.

17. An assembly according to claim 13 wherein the electrically conductive material comprises foil affixed to the wall.

18. An assembly according to claim 13 wherein the electrically conductive material comprises material located within the wall.

19. An assembly according to claim 18 wherein the electrically conductive material comprises an electrically conductive shell on the wall.

20. An assembly according to claim 13 and further including a radiopaque material carried by the structure.

21. A folding electrode assembly comprising
a structure comprising a wall peripherally enclosing an interior, the structure adapted to selectively assume a geometry that changes between an expanded geometry having a first maximum diameter and a collapsed geometry having a second maximum diameter less than the first maximum diameter, and
at least two spaced apart coatings of electrically conductive material applied to the wall adapted for transmitting ablation energy, the coatings conforming to both the expanded geometry and the collapsed geometry, the coatings being spaced apart by a predetermined distance (x) that, taking into account thickness (t) of the coatings, defines a folding region having a desired minimum fold angle (2a) when the structure is in its collapsed geometry, expressed as follows:

$$x \geq \frac{2t}{\tan \alpha}$$

22. An assembly according to claim 21 wherein the electrically conductive material of the coatings has resistivity, and wherein the folding region has resistivity that is greater than about ten times the resistivity of the electrically conductive material.

23. An assembly according to claim 21 wherein the folding region is essentially free of electrically conductive material.

24. An assembly according to claim 21 wherein the folding region includes an electrical insulating material.

25. An assembly according to claim 21 and further including at least one temperature sensing element on the structure located proximal to where electrically conductive material of at least one coating adjoins the folding region.

26. An assembly according to claim 21 and further including at least one temperature sensing element located proximal to where the electrically conductive material of at least one of the coatings adjoins the folding region.

27. An assembly according to claim 21 and further including at least one temperature sensing element on the structure located in the folding region.

28. An assembly according to claim 21 and further including at least one temperature sensing element on the structure located in the electrically conductive material of at least one of the coatings.

29. An assembly according to claim 21 and further including at least one temperature sensing element on the structure located where the electrically conductive material of at least one of the coatings adjoins the folding region.

30. An assembly according to claim 21 wherein the wall contains electrically conductive material.

31. An assembly according to claim 21 and further including a radiopaque material carried by the structure.

32. A folding electrode assembly comprising
a structure comprising a wall peripherally enclosing an interior, the structure adapted to selectively assume a geometry that changes between an expanded geometry having a first maximum diameter and a collapsed geometry having a second maximum diameter less than the first maximum diameter,
at least two spaced apart zones of electrically conductive material carried by the wall adapted for transmitting ablation energy, the electrically conductive material in the at least two zones conforming to both the expanded geometry and the collapsed geometry, and
an array of apertures in the wall between the spaced apart zones defining a folding region adapted to fold upon itself along a predefined fold line as the structure geometry changes.

33. An assembly according to claim 32 wherein the electrically conductive material has resistivity, and wherein the folding region has resistivity that is greater than about ten times the resistivity of the electrically conductive material.

34. An assembly according to claim 32 wherein the folding region is essentially free of electrically conductive material.

35. An assembly according to claim 32 wherein the folding region includes an electrical insulating material.

36. An assembly according to claim 32
and further including at least one temperature sensing element on the structure located proximal to where electrically conductive material of at least one of the zones adjoins the folding region.

37. An assembly according to claim 32
and further including at least one temperature sensing element located proximal to where the electrically conductive material of at least one of the zones adjoins the folding region.

38. An assembly according to claim 32
and further including at least one temperature sensing element on the structure located in the folding region.

39. An assembly according to claim 32
and further including at least one temperature sensing element on the structure located in the electrically conductive material of at least one of the zones.

40. An assembly according to claim 32
and further including at least one temperature sensing element on the structure located where the electrically conductive material of at least one of the zones adjoins the folding region.

41. An assembly according to claim 32
wherein the wall contains electrically conductive material.

42. An assembly according to claim 32
and further including a radiopaque material carried by the structure.

43. An assembly according to claim 32
and further including a lumen to conduct fluid into the interior for passage through the apertures to cool the at least two spaced apart zones.

44. An assembly according to claim 1 or 13 or 21 or 32
wherein the structure includes a body inflatable in response to internal fluid pressure to assume the expanded geometry, the body assuming the collapsed geometry in the absence of internal fluid pressure.

45. An assembly according to claim 1 or 13 or 21 or 32
wherein the structure includes an array of support members assembled to normally assume the expanded geometry, the structure adapted to be compressed into the collapsed geometry in response to exterior force upon the support members.

46. An assembly for ablating heart tissue comprising
a catheter tube having a distal end,
a return electrode, and
a folding electrode assembly comprising a wall peripherally enclosing an interior, the structure adapted to selectively assume a geometry that changes between an expanded geometry having a first maximum diameter and a collapsed geometry having a second maximum diameter less than the first maximum diameter, at least two spaced apart zones of electrically conductive material coupled to the return electrode and carried by the wall adapted for transmitting ablation energy, the electrically conductive material in the at least two zones conforming to both the expanded geometry and the collapsed geometry,
an array of apertures in the wall between the spaced apart zones defining a folding region adapted to fold upon itself along a predefined fold line as the structure geometry changes, and
a lumen to conduct fluid into the interior for passage through the apertures to cool the at least two spaced apart zones.

47. A method for heating body tissue comprising the steps of
providing a catheter tube having a distal end that carries a foldable electrode assembly according to claim 1 or 13 or 21 or 32,
electrically coupling a source of radio frequency energy to the electrically conductive material and to a return electrode in contact with body tissue,
guiding the catheter tube into a body while causing the foldable electrode assembly to fold about the fold line to assume the collapsed geometry,
causing the foldable electrode assembly to assume the expanded geometry in association with body tissue, and
ohmically heating body tissue by transmitting radio frequency energy through the electrically conductive material from the source to the return electrode.

48. A method for ablating body tissue comprising the steps of
providing a catheter tube having a distal end that carries a foldable electrode assembly according to claim 1 or 13 or 21 or 32,
electrically coupling a source of radio frequency energy to the electrically conductive material and to a return electrode in contact with body tissue,
guiding the catheter tube into a body while causing the foldable electrode assembly to fold about the folding region to assume the collapsed geometry,
causing the foldable electrode assembly to assume the expanded geometry in association with body tissue, and
ohmically ablating body tissue by transmitting radio frequency energy through the electrically conductive material from the source to the return electrode.

49. A method for ablating heart tissue comprising the steps of
providing a catheter tube having a distal end that carries a foldable electrode assembly according to claim 1 or 13 or 21 or 32,
electrically coupling a source of radio frequency energy to the electrically conductive material and to a return electrode in contact with body tissue,
guiding the catheter tube into a heart chamber while causing the folding electrode assembly to fold about the fold line to assume the collapsed geometry,
causing the folding electrode to assume the expanded geometry in association with heart tissue, and
ohmically ablating heart tissue by transmitting radio frequency energy through the electrically conductive material from the source to the return electrode.

50. A method for ablating heart tissue comprising the steps of
providing a catheter tube having a distal end that carries a foldable electrode assembly according to claim 32,
electrically coupling a source of radio frequency energy to the electrically conductive material and to a return electrode in contact with body tissue,
guiding the catheter tube into a heart chamber while causing the foldable electrode assembly to fold about the fold line to assume the collapsed geometry,
causing the foldable electrode assembly to assume the expanded geometry in association with heart tissue,
ohmically ablating heart tissue by transmitting radio frequency energy through the electrically conductive material from the source to the return electrode, and
conducting a cooling fluid through the array of apertures.

* * * * *